US010036698B2

(12) United States Patent
Yamamoto et al.

(10) Patent No.: US 10,036,698 B2
(45) Date of Patent: Jul. 31, 2018

(54) TIME-SEQUENTIAL CYTOMETRY

(71) Applicant: CAPTL LLC, West Lafayette, IN (US)

(72) Inventors: Masanobu Yamamoto, West Lafayette, IN (US); J. Paul Robinson, West Lafayette, IN (US)

(73) Assignee: CAPTL LLC, West Lafayette, IN (US)

(*) Notice: Subject to any disclaimer, the term of this patent is extended or adjusted under 35 U.S.C. 154(b) by 61 days.

(21) Appl. No.: 15/187,346

(22) Filed: Jun. 20, 2016

(65) Prior Publication Data

US 2016/0370280 A1 Dec. 22, 2016

Related U.S. Application Data

(60) Provisional application No. 62/182,033, filed on Jun. 19, 2015.

(51) Int. Cl.
*G01N 21/00* (2006.01)
*G01N 15/14* (2006.01)
*G01N 15/10* (2006.01)

(52) U.S. Cl.
CPC ....... *G01N 15/1427* (2013.01); *G01N 15/147* (2013.01); *G01N 15/1434* (2013.01);
(Continued)

(58) Field of Classification Search
CPC ........... G01N 15/1427; G01N 15/1434; G01N 15/147; G01N 15/1475; G01N 15/1404;
(Continued)

(56) References Cited

U.S. PATENT DOCUMENTS 3,918,812 A 11/1975 Holm
4,573,796 A 3/1986 Martin et al.
(Continued)

FOREIGN PATENT DOCUMENTS

EP 0950890 A2 10/1999
JP H05346390 12/1993
(Continued)

OTHER PUBLICATIONS

The Japanese Office Action dated Jun. 6, 2017 for Japanese Patent Application No. 2016-514059, a counterpart foreign application of US Pat. No. 9,372,143.
(Continued)

*Primary Examiner* — Hina F Ayub
(74) *Attorney, Agent, or Firm* — Lee & Hayes, PLLC; Christopher J. White

(57) ABSTRACT

An image flow cytometer for observing a microparticulate sample includes a flow chamber having a flow channel that permits the microparticulate sample to travel in a flow direction. An irradiation system scans an irradiation spot across a sensing area of the flow channel in a scan direction different from the flow direction. A detection system detects resultant light from the sensing area and provides a detection signal. An alignment system alters a location of the sensing area with respect to the flow chamber. A control unit causes the irradiation system to scan the irradiation spot during a first measurement interval and operates the alignment system to translate the location of the sensing area along the flow direction. The flow chamber can be mounted to a movable stage in some examples, and the alignment system can move the flow chamber substantially opposite the flow direction using the stage.

20 Claims, 21 Drawing Sheets

(52) U.S. Cl.
CPC ..... *G01N 15/1475* (2013.01); *G01N 15/1404* (2013.01); *G01N 2015/1006* (2013.01); *G01N 2015/144* (2013.01); *G01N 2015/1409* (2013.01); *G01N 2015/1413* (2013.01); *G01N 2015/1452* (2013.01)

(58) Field of Classification Search
CPC ... G01N 2015/1006; G01N 2015/1409; G01N 2015/1413; G01N 2015/144; G01N 2015/1452
USPC .......................................................... 356/72
See application file for complete search history.

(56) References Cited

U.S. PATENT DOCUMENTS

| | | | |
|---|---|---|---|
| 4,920,275 | A | 4/1990 | Itoh |
| 4,999,513 | A | 3/1991 | Ito et al. |
| 5,017,497 | A | 5/1991 | Gerard De Grooth et al. |
| 5,294,806 | A | 3/1994 | Batchelder et al. |
| 5,644,388 | A | 7/1997 | Maekawa et al. |
| 5,793,485 | A | 8/1998 | Gourley |
| 5,824,269 | A | 10/1998 | Kosaka et al. |
| 6,159,739 | A | 12/2000 | Weigl et al. |
| 6,249,341 | B1 | 6/2001 | Basiji et al. |
| 6,608,680 | B2 | 8/2003 | Basiji et al. |
| 6,642,018 | B1 | 11/2003 | Koller et al. |
| 6,763,149 | B2 | 7/2004 | Riley et al. |
| 6,856,390 | B2 | 2/2005 | Nordman et al. |
| 7,016,022 | B2 | 3/2006 | Fritz et al. |
| 7,113,266 | B1 * | 9/2006 | Wells ................ G01N 15/1404 356/336 |
| 7,190,832 | B2 | 3/2007 | Frost et al. |
| 7,315,357 | B2 | 1/2008 | Ortyn et al. |
| 7,522,758 | B2 | 4/2009 | Ortyn et al. |
| 7,634,125 | B2 | 12/2009 | Ortyn et al. |
| 7,634,126 | B2 | 12/2009 | Ortyn et al. |
| 7,800,742 | B2 | 9/2010 | Fukuda et al. |
| 7,800,754 | B2 | 9/2010 | Kenyon |
| 7,804,594 | B2 | 9/2010 | Vacca et al. |
| 7,925,069 | B2 | 4/2011 | Ortyn et al. |
| 8,131,053 | B2 | 3/2012 | Ortyn et al. |
| 8,159,670 | B2 | 4/2012 | Vacca et al. |
| 8,400,632 | B2 | 3/2013 | Vacca et al. |
| 8,406,498 | B2 | 3/2013 | Ortyn et al. |
| 8,548,219 | B2 | 10/2013 | Ortyn et al. |
| 8,660,332 | B2 | 2/2014 | Ortyn et al. |
| 2002/0030811 | A1 | 3/2002 | Schindler |
| 2002/0113204 | A1 | 8/2002 | Wang et al. |
| 2002/0123033 | A1 | 9/2002 | Eyal et al. |
| 2003/0007894 | A1 | 1/2003 | Wang et al. |
| 2004/0067167 | A1 | 4/2004 | Zhang et al. |
| 2004/0266022 | A1 | 12/2004 | Sundararajan et al. |
| 2005/0046848 | A1 | 3/2005 | Cromwell et al. |
| 2005/0057749 | A1 | 3/2005 | Dietz et al. |
| 2005/0068536 | A1 | 3/2005 | Schwabe |
| 2005/0122522 | A1 | 6/2005 | Padmanabhan et al. |
| 2007/0109530 | A1 | 5/2007 | Ueno et al. |
| 2007/0171778 | A1 | 7/2007 | Saito et al. |
| 2009/0122311 | A1 | 5/2009 | Kanda |
| 2009/0201504 | A1 | 8/2009 | Ho et al. |
| 2009/0298703 | A1 | 12/2009 | Gough et al. |
| 2010/0021039 | A1 | 1/2010 | Ortyn et al. |
| 2010/0120077 | A1 | 5/2010 | Daridon |
| 2010/0172020 | A1 | 7/2010 | Price et al. |
| 2010/0231913 | A1 | 9/2010 | Tsukii et al. |
| 2010/0238442 | A1 | 9/2010 | Heng et al. |
| 2011/0066382 | A1 | 3/2011 | Adams |
| 2011/0069310 | A1 | 3/2011 | Muraki et al. |
| 2011/0085221 | A1 | 4/2011 | Ortyn et al. |
| 2011/0169837 | A1 | 7/2011 | Takata et al. |
| 2011/0192991 | A1 | 8/2011 | Fukumoto et al. |
| 2011/0216319 | A1 | 9/2011 | Schwabe |
| 2012/0070818 | A1 | 3/2012 | Rowlen et al. |
| 2012/0103112 | A1 | 5/2012 | Vrane et al. |
| 2012/0136584 | A1 | 5/2012 | Ban et al. |
| 2012/0139917 | A1 | 6/2012 | Suzuki et al. |
| 2012/0220022 | A1 | 8/2012 | Ehrlich et al. |
| 2012/0270306 | A1 | 10/2012 | Vacca et al. |
| 2012/0281216 | A1 | 11/2012 | Ilkov |
| 2012/0287435 | A1 | 11/2012 | Adams et al. |
| 2012/0293797 | A1 | 11/2012 | Braeckmans et al. |
| 2012/0295339 | A1 | 11/2012 | Wu et al. |
| 2013/0050782 | A1 | 2/2013 | Heng et al. |
| 2013/0091937 | A1 | 4/2013 | Rich |
| 2014/0339446 | A1 | 11/2014 | Yamamoto et al. |
| 2014/0353522 | A1 * | 12/2014 | Wu ..................... G01N 15/1434 250/458.1 |

FOREIGN PATENT DOCUMENTS

| | | |
|---|---|---|
| JP | H05346392 | 12/1993 |
| JP | 2005291831 | 10/2005 |
| JP | 2009063308 | 3/2009 |
| JP | 2013502590 | 1/2013 |
| WO | WO03016875 A2 | 2/2003 |
| WO | WO2007121179 A2 | 10/2007 |
| WO | WO2013054502 A1 | 4/2013 |

OTHER PUBLICATIONS

Sundararajan, et al., "Three-Dimensional Hydrodynamic Focusing in Polydimethylsiloxane (PDMS) Microchannels", Journal of Microelectromechanical Systems, vol. 13, No. 4, Aug. 1, 2004, IEEE, pp. 559-567.

Doohan, James, "Blood Cells," retrieved on Feb. 12, 2016, at <<http://www.biosbcc.net/doohan/sample/htm/Blood%20cells.htm>>, Biological Sciences BioMed 108 Human Physiology, 2000, 6 pages.

Eisert, W.G., "High Resolution Optics Combined with High Spatial Reproducibility in Flow", Cytometry, vol. 1, No. 4, Jan. 1981, pp. 254-259.

Focusing and Collimating, retrieved on Dec. 4, 2015, at <<http://www.newport.com/Focusing-and-Collimating/141191/1033/content.aspx>>, Newport, 3 pages.

Goda et al., "Hybrid Dispersion Laser Scanner", in the Journal of Scientific Reports, vol. 2, Jun. 8, 2012, pp. 1-8.

Kim, et al., "An efficient 3-dimensional hydrodynamic focusing microfluidic device by means of locally increased aspect ratio", Microelectronic Engineering, vol. 86, No. 4-6, Apr. 1, 2009, Elsevier Publishers, pp. 1343-1346.

Koller et al., "High-Throughput Laser-Mediated In Situ Cell Purification With High Purity and Yield", Cytometry Part A, No. 61, Oct. 2004, pp. 153-161.

Kumbhakar et al., "Single-Molecule Detection in Exploring Nanoenvironments: An Overview", Abstract of, in the Journal of Photochemistry and Photobiology C: Photochemistry Reviews, vol. 5, Iss. 2, Oct. 15, 2004, pp. 113-137, available at <<http://www.sciencedirect.com/science/article/pii/S1389556704000206>>, 3 pages.

Mahon, et al., "Blood Cell Identification," retrieved on Dec. 4, 2015, at <<http://www.depts.ttu.edu/liru_afs/staff/dailey/jwdblood.htm>>, 1 page.

Mullaney et al., "Cell Sizing: A Light Scattering Photometer for Rapid Volume Determination,"In the Review of Scientific Instruments, vol. 40, No. 8, Aug. 1969, 5 pages.

Office Action for U.S. Appl. No. 13/894,521, dated Sep. 17, 2015, Yamamoto et al., "Scanning Image Flow Cytometer", 12 pages.

PCT Search Report and Written Opinion dated Apr. 13, 2016 for PCT application No. PCT/US2015/066947, 12 pages.

PCT Search Report and Written Opinion dated Sep. 26, 2014 for Application No. PCT/US2014/037995, 11 pages.

PCT Search Report and Written Opinion dated Sep. 14, 2015 for PCT Application No. PCT/US14/71391, 15 pages.

Simonnet, et al., "Two-dimensional hydrodynamic focusing in a simple microfluidic device", Applied Physics Letters, American Institute of Physics, US, vol. 87, No. 11, Sep. 8, 2005, pp. 114104-1 to 114104-3.

(56) References Cited

OTHER PUBLICATIONS

Spectra-Physics: SP-120 Manual, retrieved on Dec. 4, 2015, at <<https://web.archive.org/web/20041227095059/http://lasers.757.org/manuals/Spectra_Physics_120-256/p44.JPG>>, 12 pages.

Vacca et al., "Laser Rastering Flow Cytometry: Fast Cell Counting and Identification", in the Proceedings of SPIE BiOS: Biomedical Optics, International Society for Optics and Photonics, Feb. 2009, 11 pages.

van Dilla, et al., "Cell Microfluorometry: A Method for Rapid Fluorescence Measurement," Science, vol. 163, No. 3872, Mar. 14, 1969, pp. 1213-1214.

Zeiss, Carl, "LSM 710—The Power of Sensitivity—A New Dimension in Confocal Laser Scanning Microscopy," 0775 Jena, Germany, BioSciences, microscopy@zeiss.com(www.zeiss.com/microscopy), May 2009, 32 pages.

Zhuang, et al., "Detection of unlabeled particles in the low micrometer size range using light scattering and hydrodynamic 3D focusing in a microfluidic system", Electrophoresis, vol. 33, No. 12, Jul. 28, 2012, pp. 1715-1722.

* cited by examiner

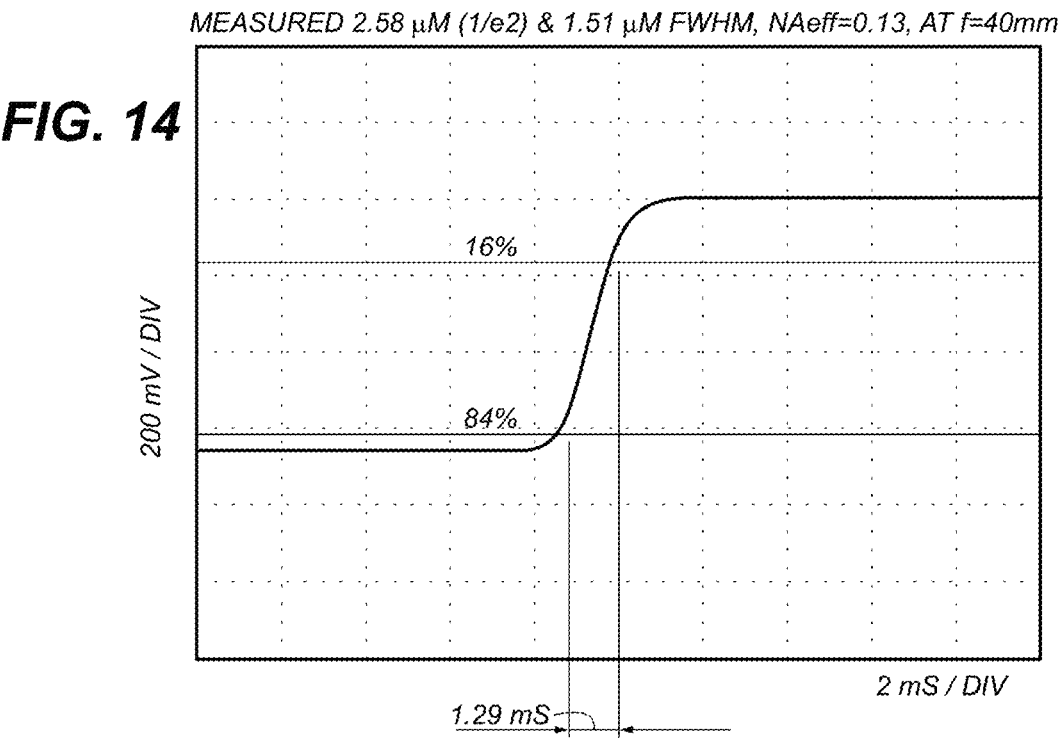
FIG. 14 — MEASURED 2.58 μM (1/e2) & 1.51 μM FWHM, NAeff=0.13, AT f=40mm
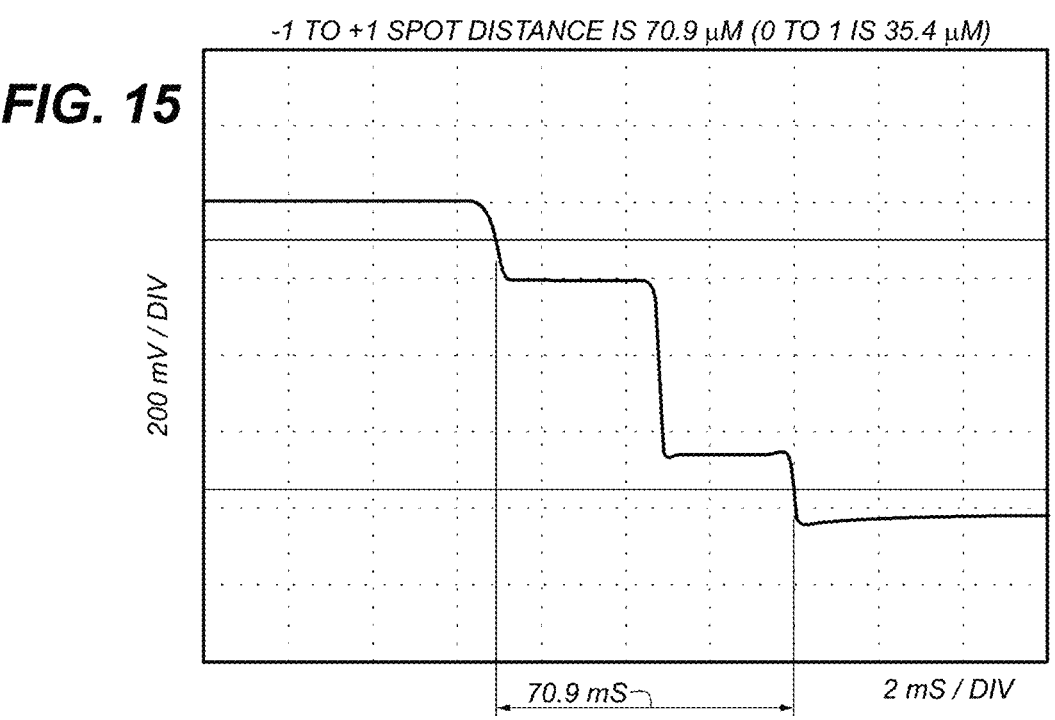
FIG. 15 — -1 TO +1 SPOT DISTANCE IS 70.9 μM (0 TO 1 IS 35.4 μM)

TIME-SEQUENTIAL CYTOMETRY

CROSS-REFERENCE TO RELATED APPLICATIONS

This application is a nonprovisional application of, and claims priority to and the benefit of, U.S. patent application Ser. No. 62/182,033, filed Jun. 19, 2015 and entitled "Time-Sequential Cytometry," the entirety of which is incorporated herein by reference.

TECHNICAL FIELD

The present application relates to flow cytometry, and particularly to image flow cytometry.

BACKGROUND

In the fields related to life sciences such as genetics, immunology, molecular biology, and environmental science, flow cytometry is widely used to analyze microparticulate samples such as living cells, yeast, and bacteria. Particles or cells from 500 nm up to 50 micron can generally be measured in flow cytometry. In general, in the case of analyzing a cell or the like with a flow cytometer, a label made of a fluorescent substance is attached to the surface of a cell to be analyzed. Next, a liquid such as water or saline is used to move the labeled cell through a flow channel of a flow chamber, which is an area in which the labeled cell is to be analyzed, and laser light having a relatively high output is radiated towards a predetermined position to irradiate the cell. Then, forward-scattered light and side-scattered light, which are generated due to the size and structure of each cell, and fluorescence, which is generated by excitation light irradiation, are observed. In the case of observing fluorescence from a cell, a configuration for spectral analysis of the fluorescence condensed in a direction other than an irradiation path of excitation light is widely used to avoid adverse effects of transmitted or scattered excitation light. Fluorescent substances to be attached or combined for each type of cells are known. Accordingly, the wavelength and intensity of the fluorescence are observed and the intensity component to be superimposed is compensated to thereby identify the type of each cell flowing through the flow channel.

Some flow cytometers perform measurement of cells or the like with laser light. A large number of microparticulate samples are supplied to a flow chamber through a tube from a container such as a vial containing the samples. The flow chamber is generally configured to permit microparticulate samples to be aligned and flow by a method called hydrodynamic focusing.

BRIEF DESCRIPTION OF THE DRAWINGS

Objects, features, and advantages of the present invention will become apparent in the following description and drawings wherein identical reference numerals have been used, where possible, to designate identical features that are common to the figures.

FIG. 14 shows measured data of an optical system.

FIG. 15 shows measured data of an optical system.

Figure 1:
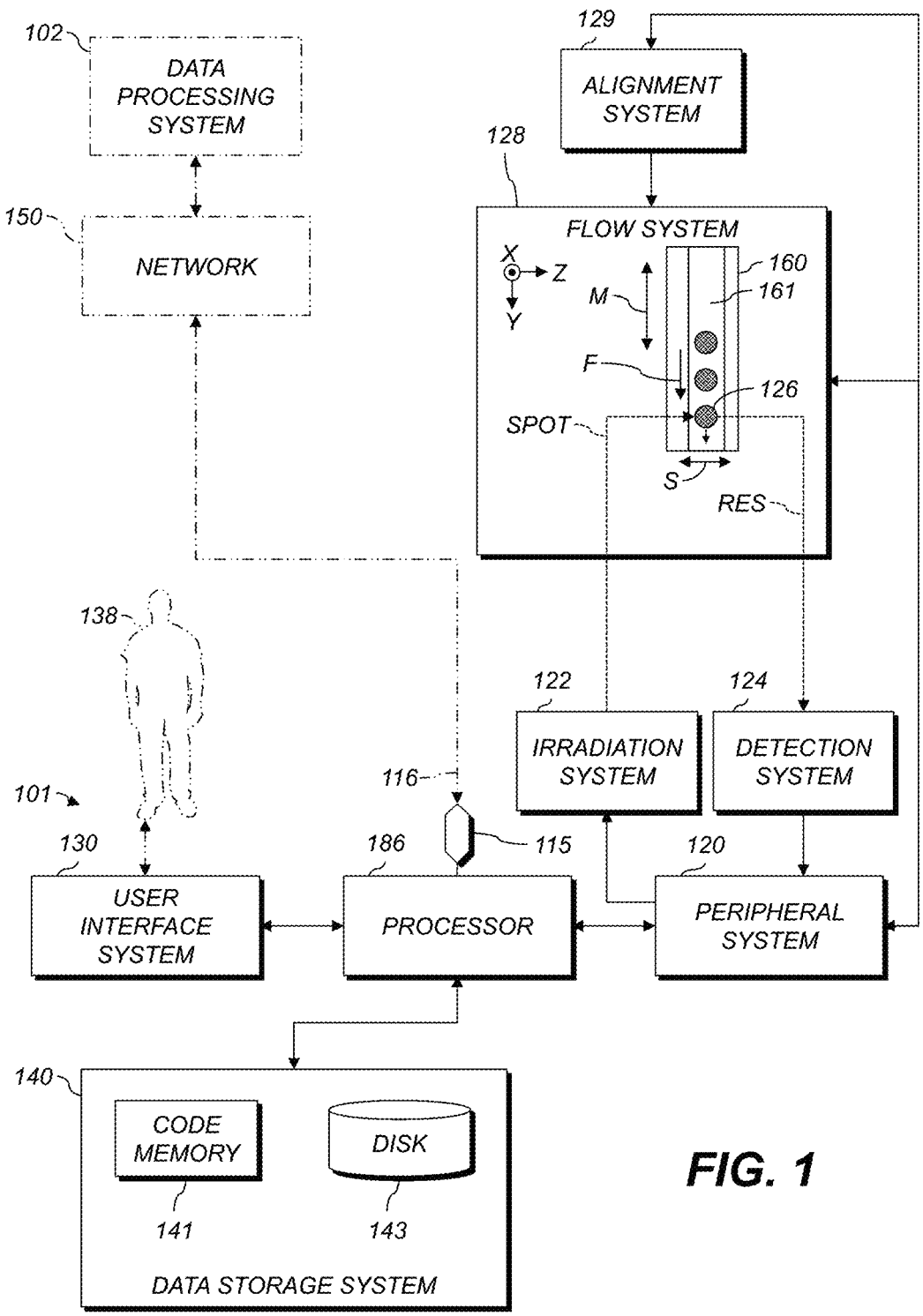
FIG. 1 shows components of an image flow cytometer for observing a microparticulate sample, and related components, including high-level components of a data-processing system.

The attached drawings are for purposes of illustration and are not necessarily to scale.

DETAILED DESCRIPTION

Overview

Reference is made to the following, each of which is incorporated by reference in its entirety: U.S. patent application Ser. No. 13/894,521, International Application Number PCT/US14/71391, and U.S. Provisional Patent Application Ser. No. 62/094,322.

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Flow cytometers using hydrodynamic focusing provide a sample flow including a carrier fluid in which are suspended or dispersed microparticulate samples. The sample flow can be, e.g., discharged from an elongated nozzle. The discharged sample flow is surrounded by a sheath flow of, e.g., water or saline, which is an isosmotic fluid, and flows through the flow channel of the flow chamber. The discharge pressure of the sample flow is set to be higher than that of the sheath flow, thereby permitting the microparticulate samples, which are randomly distributed, to be aligned and flow in the sample flow. This phenomenon is called a three-dimensional (3-D) laminar flow in terms of fluid dynamics. This makes it possible to radiate laser light independently towards each microparticulate sample, such as a cell, and to detect and analyze the scattered light and excited fluorescence.

Next, a typical flow cytometry system ("flow cytometer") will be described. A typical flow cytometer includes a laser light irradiation optical system, a flow chamber, a detection optical system, and a control unit. The laser light irradiation optical system radiates laser light onto microparticulate samples within the flow chamber. The laser light irradiation optical system includes one or more lasers that output laser light having a wavelength corresponding to a label to be excited, and a condensing optical system that condenses the laser light on the flow chamber. The detection optical system can detect an intensity of light such as transmitted light, scattered light, and fluorescence from the microparticulate samples.

When the flowing microparticulate samples pass through laser irradiation spots, scattered light and fluorescence, which is caused due to excitation of a labeled substance, are generated. The scattered light includes forward-scattered light having a small scattering angle which represents a size of a fine particle, and side-scattered light having a large scattering angle which represents an internal structure of a fine particle. Each of the forward-scattered light, the side-scattered light, and the fluorescence is detected by a photo-detector of the detection optical system. The fluorescence has a small intensity and is radiated uniformly over the whole solid angle. For this reason, the fluorescence is condensed by a condenser lens having a large numerical aperture, and is then detected by an ultrasensitive photodetector which is called a photomultiplier tube (PMT). Then, the control unit performs amplification, analog-digital conversion, and operation on the light signal detected by the photodetector.

Various aspects include a flow cytometer including a mechanism for fractional extraction (sorting) of microparticulate samples such as cells. In some examples, an ultrasonic vibration is applied to a stream in the flow chamber to thereby divide the stream, which is discharged from the orifice, into droplets, so that each droplet contains the microparticulate sample. Then, based on the measurement by the control unit, positive or negative electric charges are applied to the droplets. The droplets having positive or negative electric charges are deflected in the opposite direction depending on the polarity of the electric charges, when passing through a high-intensity electric field. After that, the deflected droplets are collected. As a result, sorted cells can be extracted for each type, and only cells of a specific type selected for analysis, culture, or the like can be obtained. A flow cytometer having such a fractional extraction function is called a sorter. A flow cytometer which does not have such a fractional extraction function but has only an analysis function is called an analyzer.

Some current systems detect scatter and fluorescence signal by illuminating a cell with laser spot significantly larger than the cell itself. In some examples, the laser spot has a so-called "Top-Hat" shape for uniform illumination which brings a wider tolerance by reducing the spatial resolution. In some examples, a Gaussian-profile laser beam can be used; such beams can have higher spatial resolution and peak intensity than top-hat-profile beams. Various examples provide techniques for analyzing multiple cell features (e.g., every cell feature) by using a smaller laser spot than the cells/particles being analyzed. Some examples can measure microstructures within a cell, the locations of fluorescent features within a microparticulate sample such as a cell, or the shapes of microparticulate samples, such as two-dimensional (2-D) shapes or three-dimensional (3-D) shapes. An "image cytometer" is a cytometer that can provide data relating to a spatial relationship between detected signals and cellular or particle locations. An image cytometer can use an actual imaging camera to create the spatial data, or can use other devices, e.g., as described herein. Some examples using multiple irradiation spots can image multiple microparticulate samples at a time.

Accordingly, various aspects described herein provide an image flow cytometer capable of observing a structure of each microparticulate sample. Various aspects permit doing so while maintaining a high throughput, i.e., measuring a large number of particles (or other microparticulate samples) per second. Various aspects use flying-spot technology in cytometry, e.g., using a 405 nm laser, acoustic optical (AO) device & driver, custom objective lens, high speed detectors and a huge data acquisition system. Various examples include a planar-type flow chamber design. Spot size, flow velocity, and beam deflection frequency can be determined based upon cell size and optical tolerance. Some examples use a 2 µm FWHM (full width at half maximum) laser spot, 0.1-1.0 m/s flow velocity, 0-50 µm deflection range, or 100 kHz-1000 kHz beam deflection. Using 405 nm as the wavelength of the spot (or as the shortest wavelength of the spot) has the advantage of reduced spot size and deflection RF power. 405 nm excitation can provide a broad wavelength range for fluorescence detection. Various aspects use a wavelength stabilized 405 nm laser with a planar wave front and a Gaussian profile. Beam deflection permits micro imaging. Various examples include $TeO_2$ crystals for acoustic optical (AO) high-speed beam deflection. Finite optics can be used to reduce wavefront distortion and satisfy fill conditions.

In various examples, the AO deflection frequency is 250 MHz±50 MHz. An NA=0.16 objective lens can be used. Various examples provide 40 μm (pk-pk) linear beam deflection scanning at 1 MHz. A 2.1 μm FWHM laser spot size can be used. In, e.g., a planar flow chamber, the use of a flying spot (scanning irradiation spot) permits simultaneous detection of multiple cells on the focused plane. Various flow chambers provide in-focus (hydrodynamic) flow at 0.1-1.0 m/s mean velocity using a flying spot velocity of up to 40 m/s. Various examples use 70 MHz-bandwidth detector modules. Various examples use Si PIN diodes for 405 nm signal detection and μPMTs for high speed fluorescence detection. Various examples include a data acquisition system having a 16 bit/160 MHz/4-channel A/D converter to capture high speed data. Various examples record raw data on 1.5 TB solid state memory at, e.g., 10.24 Gbps. Various examples have been tested using beads and stained cells mounted on slides and flow chambers. Various examples permit live cell analysis, e.g., to detect or analyze cell damage.

Various examples include a laser spatial resolution of, e.g., down to 0.25 microns. Various examples include ultraviolet (UV) irradiation. Various examples permit at least one of particle detection, polarization analysis, photon fluorescence, time sequential analysis, and 3D cell imaging.

Various aspects herein relate to flow cytometers, e.g., image flow cytometers that can provide information about a microparticulate sample beyond or in addition to information that the sample is present in a sensing area of a flow chamber. Flow cytometers irradiate microparticulate samples, e.g., using laser(s), and detect resultant light. The term "irradiate" herein does not require or imply any particular radiant or luminous power level.

Various aspects herein include moving the location of irradiation with respect to the flow chamber, e.g., by moving the flow chamber itself or by moving the source of irradiation or redirecting the irradiation. These aspects permit measuring a particular microparticulate sample at multiple times, e.g., over the course of a reaction between the microparticulate sample and a chemical. For example, a cell can be measured over time as it reacts to a drug. Aspects in which the flow chamber moves are in sharp contrast to various prior cytometry schemes in which the flow chamber is required to be stationary in order to provide absolute stability. Some prior schemes require absolute stability of the entire optical system for accurate and reproducible analysis. By contrast, various examples herein can provide consistent flow in the flow chamber, e.g., using hydrodynamic focusing, and can therefore move the flow chamber to provide repeated imaging of a particular sample at an acceptable image-quality level.

Various aspects scan multiple irradiation spots, e.g., 3 spots, across the flow chamber, e.g., perpendicular to the flow direction. This permits determining the flow speed of individual microparticulate samples.

Various embodiments include deflecting multiple scanning spots across, e.g., perpendicular to the flow direction (e.g., 3 spots generated by phase grating with constant distance (d) on image plane). Spot distance is dependent on optics and field of view of objective lens, e.g., 20-100 μm). In some examples, individual scanning spot(s) detect microparticulate samples and obtain time and mapping information of individual microparticulate samples. In some examples, the time difference Δt between two signals can be used to determine accurate flow velocity (v), e.g., in a micro fluidics channel. In some examples, v=d/Δt. Velocity profile in micro channel can be a parabolic profile with a peak speed substantially at channel center and substantially zero velocity at channel wall. This means velocity of a microparticle may vary depending on lateral channel location of the microparticle. Various examples include measuring the same sample using different spots to determine time dependence information between ±Δt. This can be referred to as Time Sequential Cytometry. E.g., d=50 μm, v=50 cm/s case, Δt=0.1 ms.

Various examples include Chip Displacement apparatus that moves a flow chamber at a speed higher than a flow speed or the peak speed. This can provide larger time differences or sequential time differences nΔt along flow channel length. E.g., a linear slide can be used, as discussed herein with reference to at least FIG. 11. In some examples, the microparticulate samples include live cell(s) that exhibit rapid phenomena under specific circumstance. Time-sequential cytometry permits time sequential observation on a specific cell ("Cell Tracking"). In various examples, 3 (or >1) imaging signals from respective spots can be used to generate higher resolution images in flow direction by image stitching.

Illustrative Configurations

FIG. 1 shows components of an image flow cytometer for observing a microparticulate sample, and related components. A flow chamber 160 includes a flow channel 161 formed therein to permit a microparticulate sample 126 to travel in a flow direction F along the flow channel 161.

An irradiation system 122 is adapted to scan an irradiation spot ("SPOT") across a sensing area of the flow channel 161 in at least one scan direction different from the flow direction F, e.g., along scan axis S. Light is shown dashed for clarity, and the illustrated paths are for explanation and are not limiting. The scan axis S can be transverse to the flow direction F or otherwise, e.g., at a 45° angle to the flow direction F. More than one irradiation system 122 can be present. In some examples, e.g., of a 40 μm-pp sawtooth or triangular scan at 1 MHz, the irradiation spot can be scanned at 40 m/s and measurements can be taken at 100 MHz (e.g., using an ADC sampling at 100 MHz). This combination provides a sample every ~0.4 μm. The illustrated samples 126 and irradiation spots are not shown to scale.

A detection system 124 detects a time-varying intensity of resultant light ("RES") from the sensing area and provides a corresponding detection signal. More than one detection system 124 can be present. Resultant light can include, e.g., transmitted or scattered light, or fluorescent light excited by the irradiation. Examples are discussed herein, e.g., with reference to FIG. 10.

The irradiation spot (e.g., laser light, or other light radiated into the flow channel 161), is referred to herein as "incident light." Light transmitted through the flow channel 161, or light emitted from microparticulate samples, dyes, or other substances within the flow chamber 160 or flow channel 161, is referred to herein as "resultant light." Resultant light can include forward-scattered (FS) light and side-scattered (SS) light. FS and SS have substantially the same wavelength as the light source. Resultant light can also include fluorescent light, since such light is emitted by substances within the flow channel 161. Resultant light can be substantially directional (e.g., transmitted light of the irradiation spot) or substantially omnidirectional (e.g., fluorescence).

An alignment system 129 is adapted to selectively alter a location of the sensing area with respect to the flow chamber 160. The alignment system 129 is adapted to selectively change the location of the sensing area at a speed greater than the flow rate. For example, the alignment system 129 can move the flow chamber 160. In some examples, the flow chamber 160 can be mounted on a linear slide and designed to translate, e.g., along axis M. Other examples move the irradiation spot(s) along axis M, e.g., by deflecting a laser. Examples are discussed herein, e.g., with reference to FIGS. 9-12.

In some examples, e.g., as discussed in FIG. 4, 5, or 7-10, the irradiation system 122 is adapted to scan one or more additional irradiation spot(s), e.g., three spots, across respective sensing area(s) of the flow channel 161 in respective scan direction(s) different from the flow direction F. This is referred to herein as "multiscanning," "multiple-spot scanning," and similar terms. The respective scan direction(s) can all be the same, all different, or anywhere in between. Various examples herein are described with reference to three spots, but any number ≥1 of spots can be used.

In some examples, the irradiation system 122 is adapted to scan the irradiation spot and the additional irradiation spot(s) in fixed phase with respect to each other, e.g., in phase or in fixed phases with respect to each other, e.g., for three spots, 60° or 120° apart. In some of these examples, the irradiation system 122 includes an optical element arranged to receive light from a light source and provide the irradiation spot and the additional irradiation spot(s). The optical element can include a diffractive optical element, e.g., a diffraction grating such as a phase or amplitude grating. Examples are discussed herein, e.g., with reference to FIG. 9.

In some examples, the irradiation spot is at the Rayleigh spot size, e.g., a Gaussian-profile spot having substantially zero intensity of Gaussian spot at a radius of $1.22\lambda/NA$. In some examples, the irradiation spot has a Gaussian profile and a laser spot size at 13.5% intensity of $0.82\lambda/NA$. In some examples, the irradiation spot has a FWHM (50% intensity radius) substantially equal to $0.48\lambda/NA$, e.g., $\lambda/2NA$. In some examples, the irradiation spot has a FWHM<2 μm or between $\lambda/0.1$ and $\lambda/2.0$, or between $\lambda/0.2$ and $\lambda/2.0$. These examples can be used up to NA=1.0 (the far field limit). Various aspects use NA between 1.4 and 2.0 with solid immersion lenses, or up to 1.4 with liquid immersion optics, and spot sizes $\approx\lambda/NA$. Various aspects use diffraction-limited spot sizes. In some examples, a lens is used with NA=0.16.

It is not required that all of the irradiation spot be incident on the microparticulate sample 126. For example, useful information can be gathered while scanning the irradiation spot is over the membrane of a cell, even if some of the irradiation spot is not striking the cell.

In various aspects, the irradiation spot is provided by a source other than a laser. The light source can be any source that can be focused to produce an irradiation spot smaller than the microparticulate sample to be irradiated, e.g., a lamp positioned at the focus of a parabolic reflector, or a light-emitting diode (LED) focused through a lens.

In an example, transmitted light/forward-scattered light of the resultant light is coherent light that is affected by scattering, refraction, absorption, rotation of the plane of polarization, or the like of light due to the irradiation of the laser light L onto the microparticulate samples. In some examples, the fluorescence/side-scattered light is incoherent light. Coherent side-scatter and back-scatter light can also be detected, e.g., by detection system 124. Some examples can also include measuring absorption, e.g., axial light loss. Absorption can indicate, e.g., absolute size of a microparticle or densities of microparticles.

FIG. 1 also shows components of an example data-processing system 101 for measuring microparticulate samples, analyzing data, and performing other functions described herein, and related components. The system 101 includes a processor 186, a peripheral system 120, a user interface system 130, and a data storage system 140. The peripheral system 120, the user interface system 130, and the data storage system 140 are communicatively connected to the processor 186. Processor 186 can be communicatively connected to network 150 (shown in phantom), e.g., the Internet or a leased line, as discussed below. Devices shown, e.g., in FIGS. 8, 10, and 11 can each include one or more of systems 186, 120, 130, 140, and can each connect to one or more network(s) 150.

Figure 2:
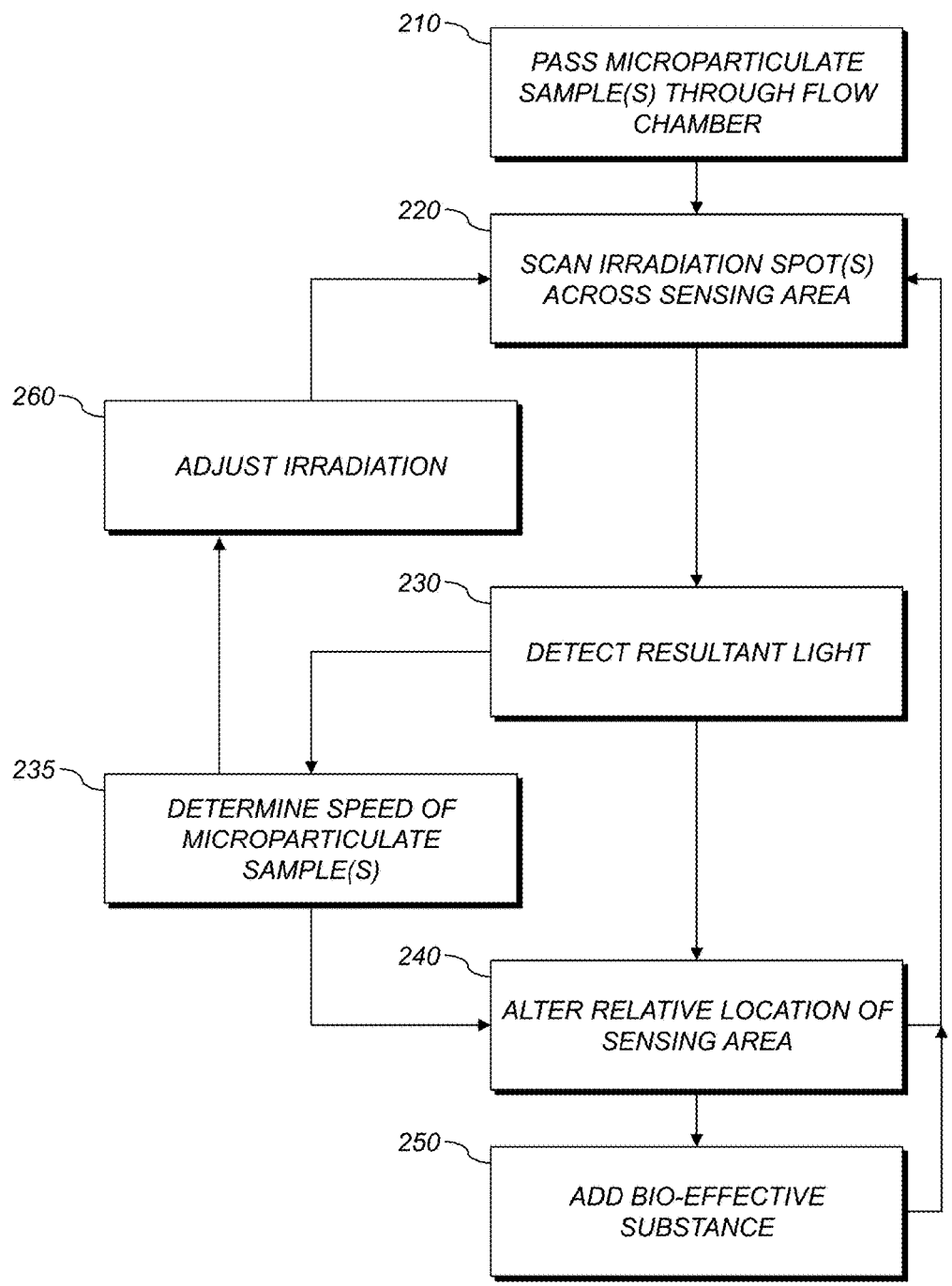
FIG. 2 is a flowchart of example methods of measuring microparticulate samples.
Figure 3:
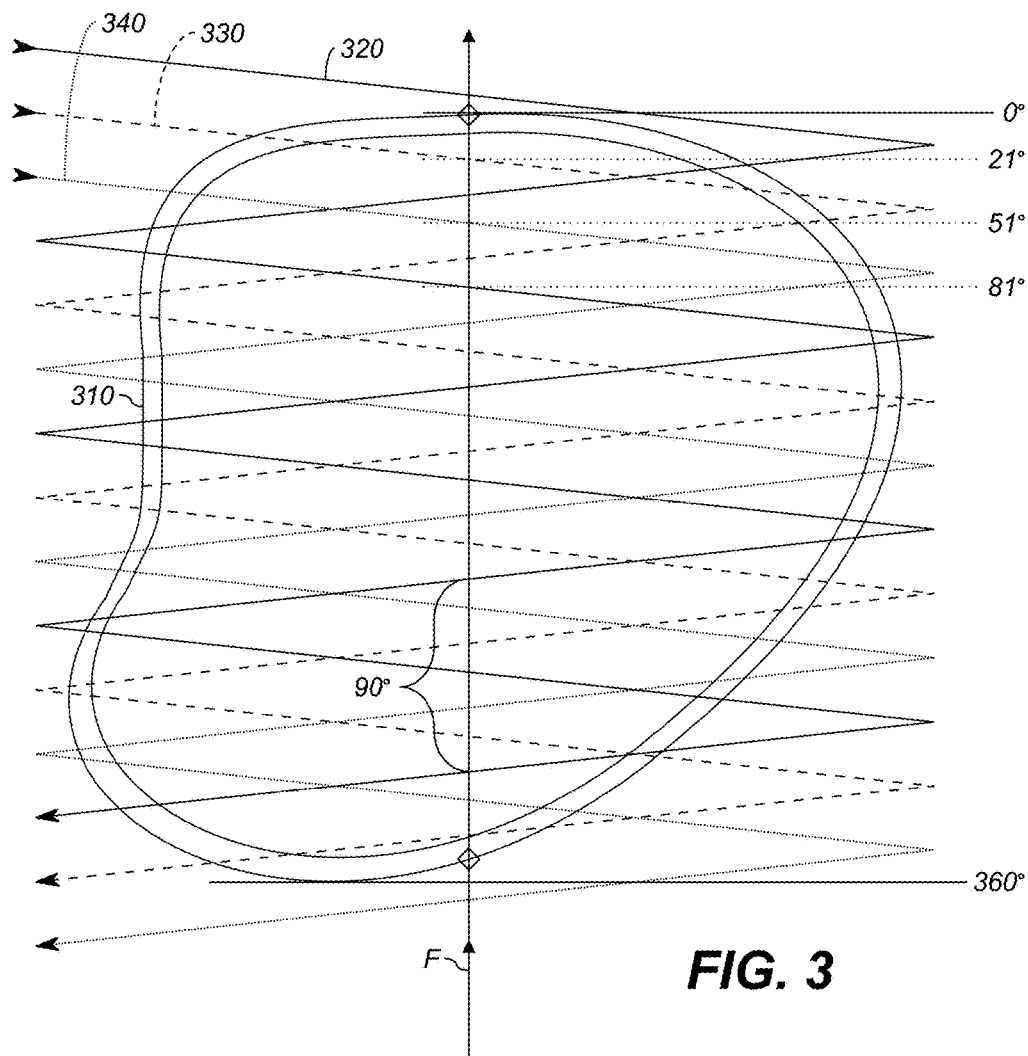
FIG. 3 shows an example of multi-scanning of a microparticulate sample.

Processor 186 can implement processes of various aspects described herein, e.g., as discussed herein with reference to FIGS. 2 and 3. Processor 186 and related components can, e.g., carry out processes for scanning multiple irradiation spots across microparticulate samples 126, for determining velocities, images, or properties of microparticulate samples 126, for translating irradiation with respect to a flow chamber 160 (e.g., by moving the flow chamber 160, e.g., along axis M, or by redirecting the irradiation), for adding bio-effective substances to a flow chamber or otherwise bringing bio-effective substances into operative association with microparticulate samples, or for measuring effects of those bio-effective substances.

In some examples, processor 186 can implement a control unit connected to the irradiation system 122, the detection system 124, and the alignment system 129 and adapted to cause the irradiation system 122 to scan the irradiation spot during a first measurement interval. The control unit can be configured to, subsequently, operate the alignment system 129 to translate the location of the sensing area along the flow direction F. The translating can be directly along the flow direction F or in any other direction having a nonzero component along the flow direction F.

Various aspects include scanning small-laser-beam cytometry, referred to as "Micro Imaging Flow Cytometry" or MIF. Some flow cytometers detect Mie scattering and spatially integrated fluorescence which is very useful for quantitative cellular analysis. Some scanning small beam cytometers provide time sequential detection from any part of cellular structure on, e.g., transmission, polarization, diffraction, and excited fluorescence. Various aspects provide time domain analysis, e.g., for cellular analysis.

Time-sequential observation of specific live cells is not possible by some conventional flow systems. Some examples herein, by contrast, use, e.g., high-speed beam-scanning with relatively slow flow velocity (e.g., less than 1 m/s) to permit such observations. Some examples use, e.g., a flow chamber mounted on a high speed linear motor slide that can move faster than cell flow. An example focused planar flow has over 20 mm of laminar flow, so it is possible to make initial observation of a targeted cell, then observe after a time delay (e.g., $n\Delta t$, discussed below, $n \in \mathbb{Z} \geq 1$). Some examples use three spaced-apart laser beams along the direction of flow to detect localized flow velocity and shorten time intervals of observation. This approach may contribute to analysis of rapid biochemical responses in a cell (or multiple cells) under exposure of reagent, temperature and ambient light, etc.

Some examples include fluorescence detection in the time-domain. In some examples, a photodetector like a micro-PMT by SiMEMS process or a SiPM as microcell APD provides single photon resolution less than 1 ns. The dark count at room temperature is significantly improved compared to previous devices. Combined with low noise and very high-speed electronics, some examples permit evaluating attowatt ($10^{-18}$ W)-level fluorescence photons with picosecond resolution. This can permit cellular and intercellular analysis, e.g., very low level fluorescence detection, photon "plotting" on cell morphology, photobleaching and resonance phenomena analysis, etc. Scanning small laser beam cytometry in the time domain according to some examples can be used for cellular and intercellular analysis, e.g., using single photon fluorescence detection.

Processor 186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs). Processor 186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 120, user interface system 130, and data storage system 140 are shown separately from the processor 186 but can be stored completely or partially within the processor 186.

The peripheral system 120 can include or be communicatively connected with one or more devices configured or otherwise adapted to provide digital content records to the processor 186 or to take action in response to processor 186. For example, the peripheral system 120 can include digital still cameras, digital video cameras, cellular phones, or other data processors. The processor 186, upon receipt of digital content records from a device in the peripheral system 120, can store such digital content records in the data storage system 140.

In the illustrated example, peripheral system 120 is communicatively connected with irradiation system 122 and detection system 124. Irradiation system 122 directs irradiation spots onto microparticulate sample 126. Detection system 124 detects resultant light from microparticulate sample 126. Processor 186 can then process the detected resultant light to, e.g., determine flow velocity of microparticulate sample 126 or determine an image of microparticulate sample 126. Peripheral system 120 can also be connected to flow system 128, e.g., to control flow rates of carrier fluid bearing or otherwise transporting microparticulate sample 126.

Figure 11:
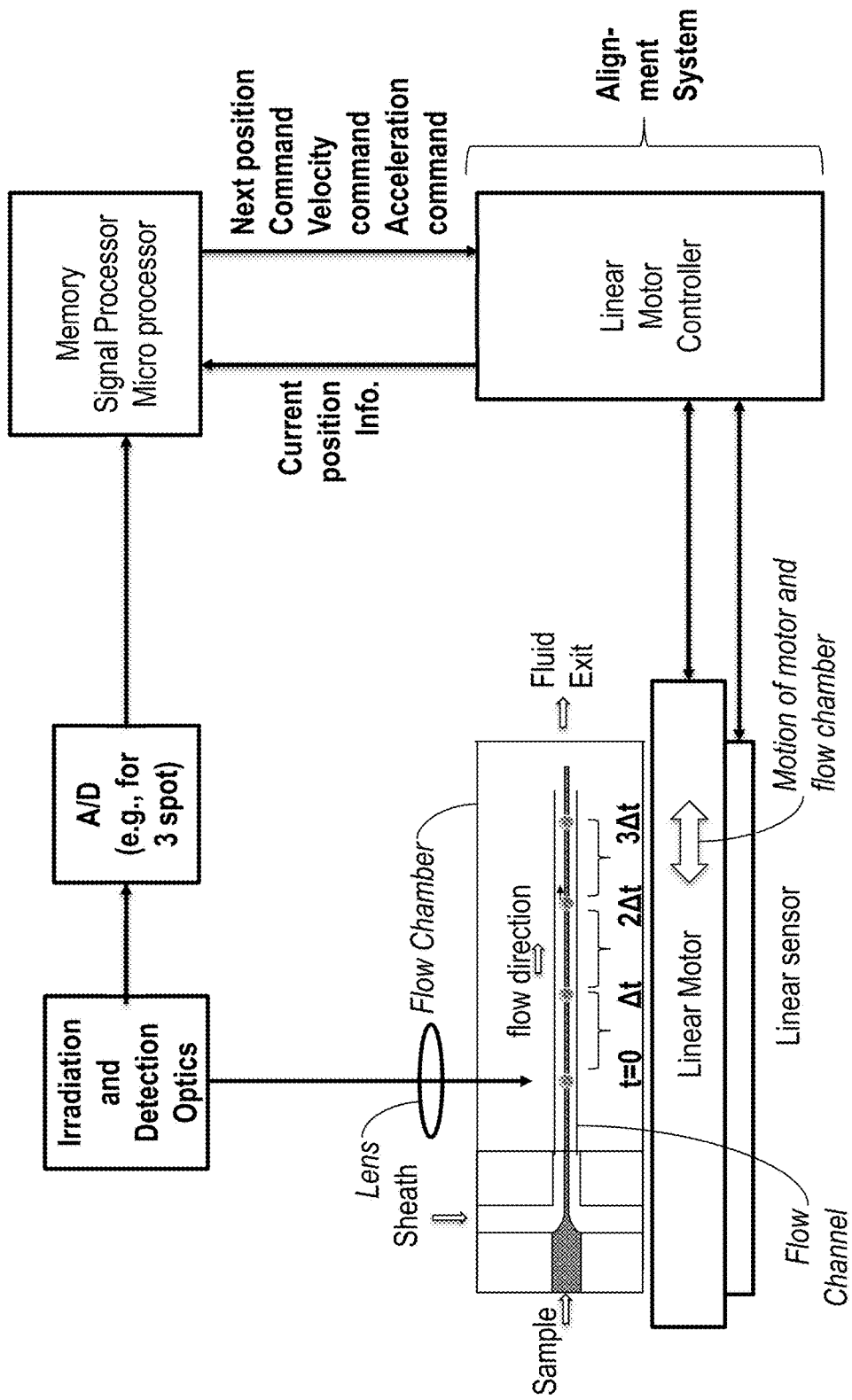
FIG. 11 shows components of an example measurement system.

In the illustrated example, peripheral system 120 is connected to alignment system 129. Alignment system 129 can change the location of irradiation by irradiation system 122 with respect to a flow chamber, e.g., as illustrated in FIG. 11 and other figures herein.

The user interface system 130 can convey information in either direction, or in both directions, between a user 138 and the processor 186 or other components of system 101. The user interface system 130 can include a mouse, a keyboard, another computer (connected, e.g., via a network or a null-modem cable), or any device or combination of devices from which data is input to the processor 186. The user interface system 130 also can include a display device, a processor-accessible memory, or any device or combination of devices to which data is output by the processor 186. The user interface system 130 and the data storage system 140 can share a processor-accessible memory.

In various aspects, processor 186 includes or is connected to communication interface 115 that is coupled via network link 116 (shown in phantom) to network 150. For example, communication interface 115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM. Communication interface 115 sends and receives electrical, electromagnetic, or optical signals that carry digital or analog data streams representing various types of information across network link 116 to network 150. Network link 116 can be connected to network 150 via a switch, gateway, hub, router, or other networking device.

In various aspects, system 101 can communicate, e.g., via network 150, with a data-processing system 102, which can include the same types of components as system 101 but is not required to be identical thereto. Systems 101, 102 are communicatively connected via the network 150. Each system 101, 102 can execute computer program instructions to carry out measurement of microparticulate samples as described herein. In some examples, system 101 can control or perform irradiation and system 102 can control or perform detection. In some examples, systems 101 and 102 can each perform irradiation and detection in different regions arranged along the flow chamber.

Processor 186 can send messages and receive data, including program code, through network 150, network link 116, and communication interface 115. For example, a server can store requested code for an application program (e.g., a JAVA applet) on a tangible non-volatile computer-readable storage medium to which it is connected. The server can retrieve the code from the medium and transmit it through network 150 to communication interface 115. The received code can be executed by processor 186 as it is received, or stored in data storage system 140 for later execution.

Data storage system 140 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 186 can transfer data (using appropriate components of peripheral system 120), whether volatile or nonvolatile; removable or fixed; electronic, magnetic, optical, chemical, mechanical, or otherwise. Example processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 140 can be a tangible non-transitory computer-readable storage medium, i.e., a non-transitory device or article of manufacture that participates in storing instructions that can be provided to processor 186 for execution.

In an example, data storage system 140 includes code memory 141, e.g., a RAM, and disk 143, e.g., a tangible computer-readable rotational storage device or medium such as a hard drive. Computer program instructions are read into code memory 141 from disk 143. Processor 186 then executes one or more sequences of the computer program instructions loaded into code memory 141, as a result performing process steps described herein. In this way, processor 186 carries out a computer implemented process. For example, steps of methods described herein, blocks of the flowchart illustrations or block diagrams herein, and combinations of those, can be implemented by computer program instructions. Code memory 141 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media may embody computer-readable instructions, data structures, program modules, or other data in a modulated data signal, such as a carrier wave or other transmission mechanism. As defined herein, computer storage media do not include communication media. That is, computer storage media do not include communications media consisting solely of a modulated data signal, a carrier wave, or a propagated signal, per se.

The program code includes computer program instructions that can be loaded into processor 186 (and possibly also other processors), and that, when loaded into processor 186, cause functions, acts, or operational steps of various aspects herein to be performed by processor 186 (or other processor). Computer program code for carrying out operations for various aspects described herein may be written in any combination of one or more programming language(s), and can be loaded from disk 143 into code memory 141 for execution. The program code may execute, e.g., entirely on processor 186, partly on processor 186 and partly on a remote computer connected to network 150, or entirely on the remote computer.

FIGS. 6 and 12-16, as well as other examples herein, show various examples of irradiation and detection systems useful with multiple irradiation spots. Some examples include optics designs, phase-grating specifications, three-spot beam deflection, and experimental results of beam spacing.

Figure 5:
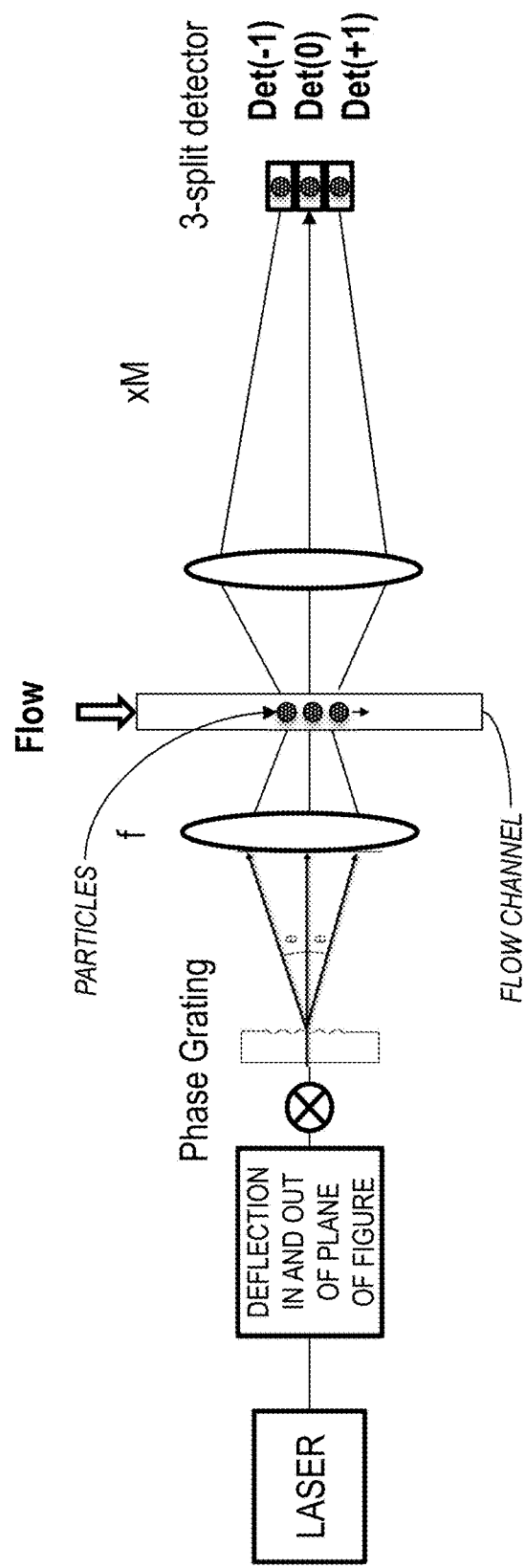
FIG. 5 shows an example measurement system for detecting or measuring properties of microparticles.
Figure 6:
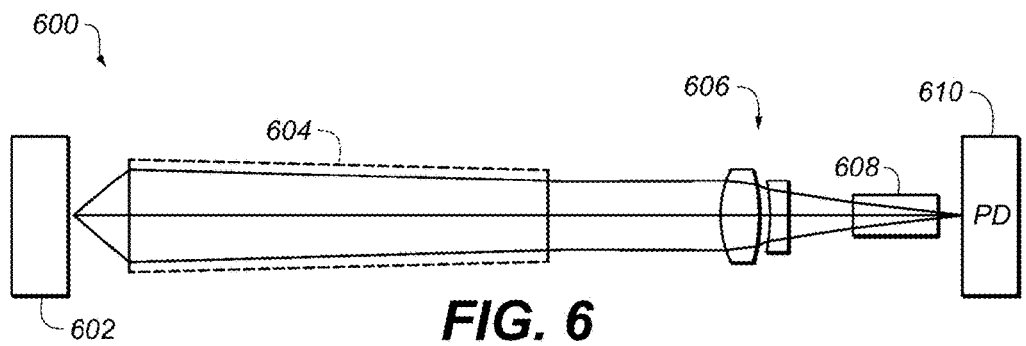
FIG. 6 shows an example optical path and components thereof.
Figure 13:
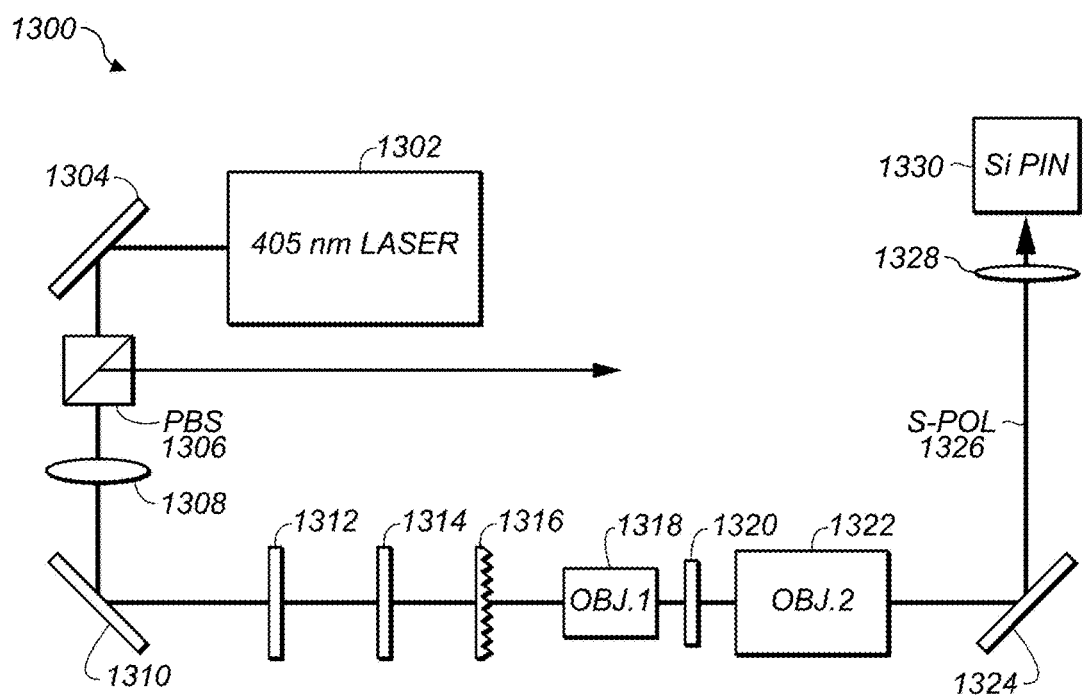
FIG. 13 shows example optical components of a measurement system.
Figure 16:
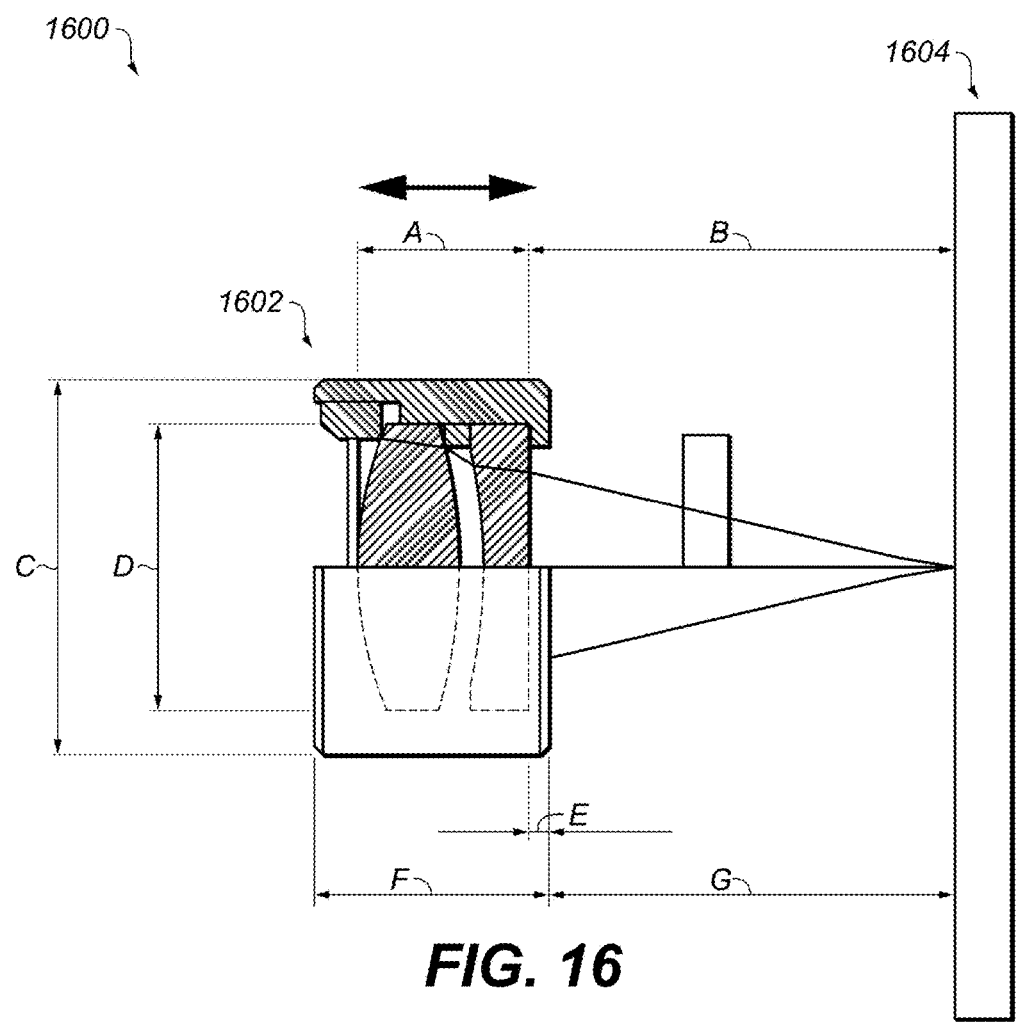
FIG. 16 shows components of an example optical system.

FIGS. 5 and 6 show example irradiation systems that can be used with other components shown in FIG. 1. FIGS. 13 and 16 show example configurations of detection systems that can be used with other components shown in FIG. 1. FIGS. 14 and 15 show experimental data of some tested examples. In some examples, a phase grating was tested having 7.2 line pairs per millimeter.

FIG. 2 shows a flowchart illustrating example methods for measuring microparticulate samples, e.g., cells. The steps can be performed in any order except when otherwise specified, or when data from an earlier step is used in a later step. In at least one example, processing begins with block 210. For clarity of explanation, reference is herein made to various components shown herein, e.g., in FIG. 1, that can carry out or participate in the steps of the example method. It should be noted, however, that other components can be used; that is, example method(s) shown in FIG. 2 are not limited to being carried out by the identified components.

At block 210, the microparticulate sample 126 or sample(s) is/are passed through a flow chamber along a flow direction.

At block 220, an irradiation spot smaller than the microparticulate sample is scanned across a sensing area of the flow chamber 160 along a scan direction (e.g., either direction along axis S, FIG. 1) different from the flow direction F. In some examples, multiple irradiation spots, individual one(s) smaller than the microparticulate sample, are scanned across respective sensing areas, e.g., as discussed herein at least with reference to FIGS. 3 and 17A-23.

At block 230, e.g., contemporaneously with scanning, a time-varying intensity of resultant light from the flow chamber is detected and a corresponding first intensity signal of the microparticulate sample is provided.

In some examples, block 230 is followed by block 235. At block 235, using a processor 186, there is determined, based at least in part on the respective first intensity signals of multiple irradiation spots, at least a lateral position of the microparticulate sample 126 or sample(s) of interest in the flow chamber or a speed of the microparticulate sample along the flow direction. Block 235 can be followed by block 240.

Figure 7:
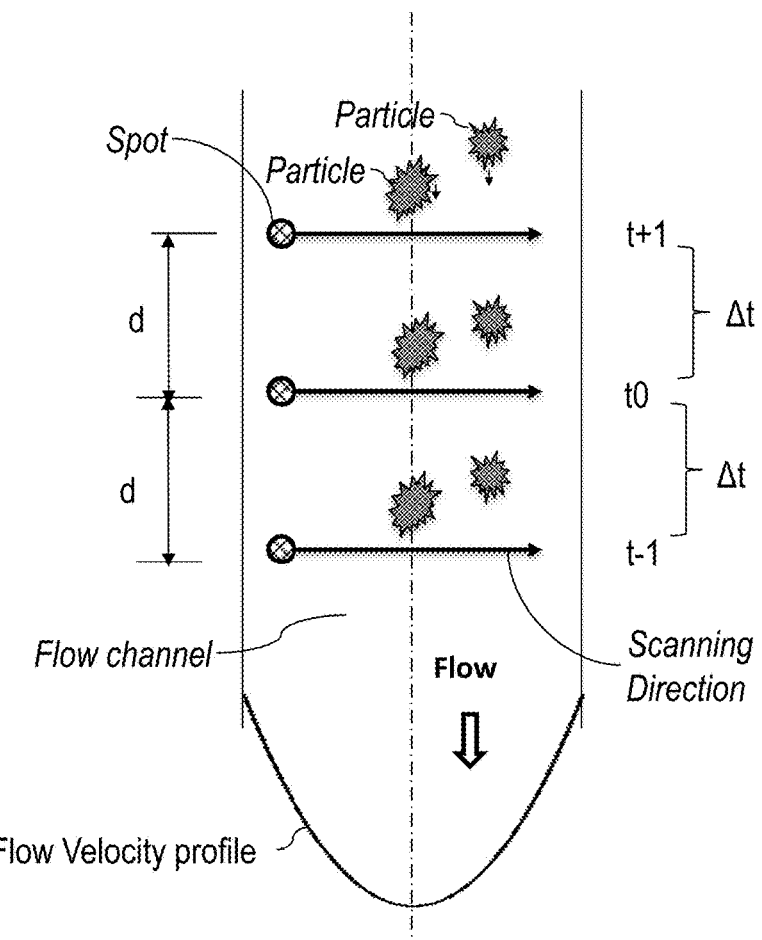
FIG. 7 shows an example of velocity measurement using multiple-spot scanning.
Figure 10:
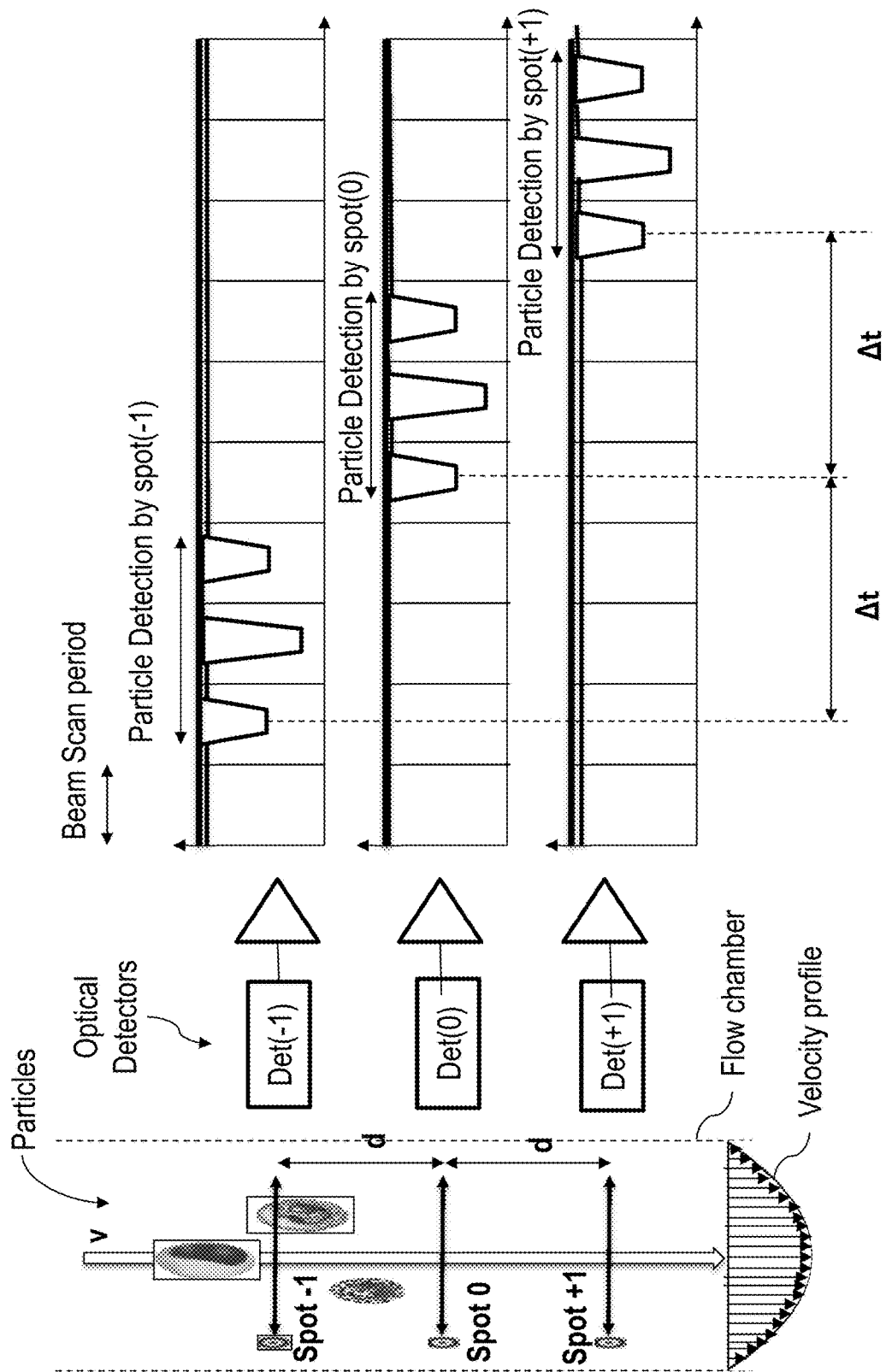
FIG. 10 shows an example of microparticle measurement.

At block 240, subsequently, a relative position of the sensing area with respect to the flow chamber is translated along the flow direction ("downstream"). Block 240 can be followed by block 220. In this way, subsequent to block 240, the scanning and detecting steps (blocks 220 and 230) can be repeated so that a second intensity signal of the microparticulate sample 126 is provided. Blocks 220, 230, and 240 can be repeated any number of times. This permits repeatedly measuring the microparticulate sample (or given one(s) of a plurality of microparticulate samples) over time. In some examples using block 235, the translating is performed at a translation speed based at least in part on the determined speed of the microparticulate sample from block 235, e.g., faster than the determined speed. This permits more accurately tracking microparticulate samples, e.g., in flow channels having nonuniform velocity profiles such as shown in FIGS. 7 and 10.

Figure 9:
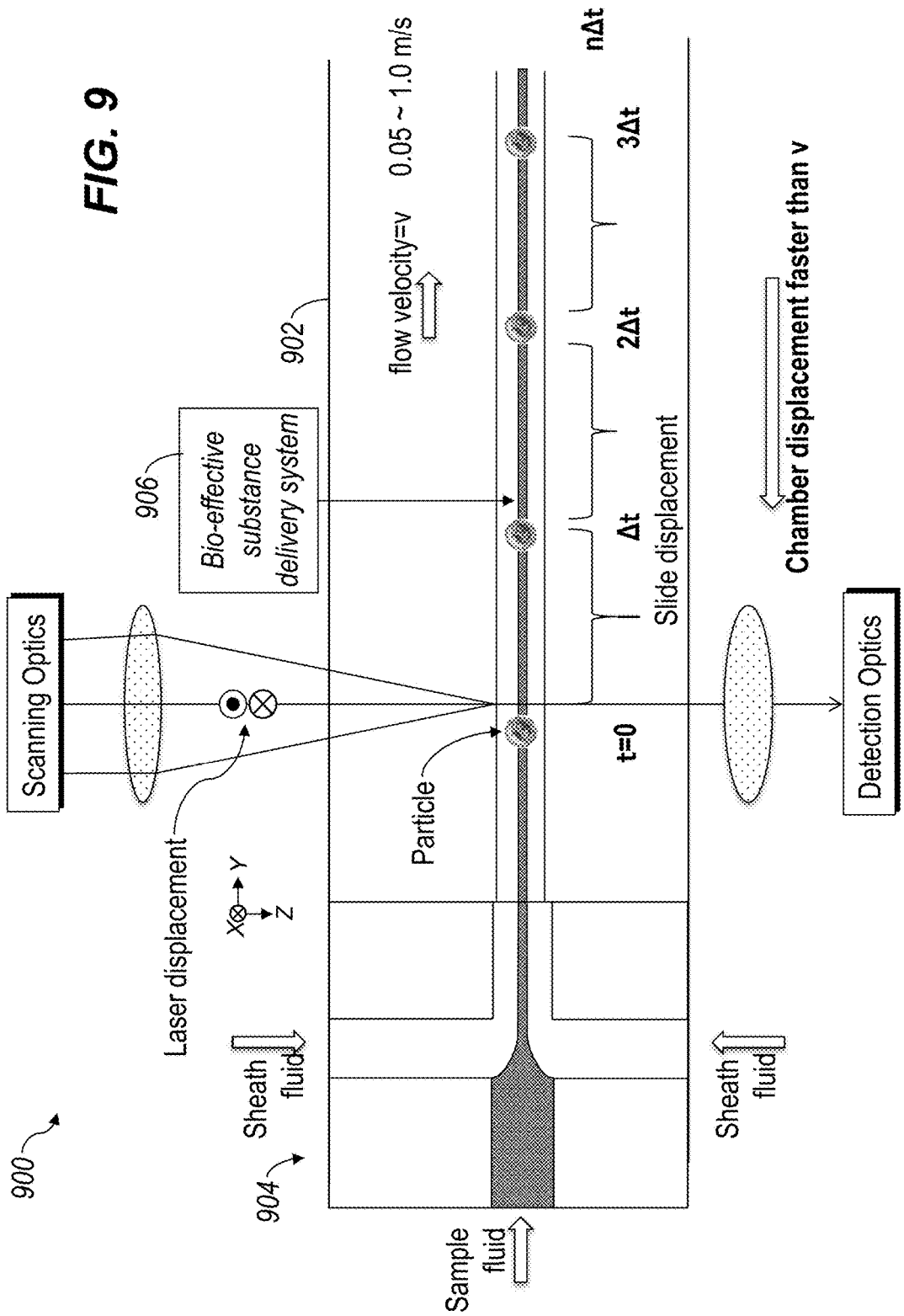
FIG. 9 shows an example of cell tracking in a flow chamber.

In some examples, block 240 is followed by block 250, which is in turn followed by block 220. In other examples, block 250 precedes block 240. At block 250, the microparticulate sample is exampled to a bio-effective substance before the repeating of the scanning step (block 220). For example, a bio-effective substance can be added to a carrier fluid that includes the microparticulate sample. Example bio-effective substances include drugs, dyes, antibodies, microbes, viruses, acids, bases, and other chemicals, substances, chemical structures, or biochemical structures that have or may have an effect on biological microparticulate samples such as cells, bacteria and other microorganisms, or viruses. This permits determining the effect over time of the bio-effective substance on the microparticulate sample. Block 250 can be repeated any number of times in accompaniment with blocks 220, 230, and 240, or separately. An example placement of an example delivery system for a microparticulate sample is shown in FIG. 9.

In some examples, block 235 is followed by block 260. At block 260, at least a scanning frequency of the plurality of irradiation spots or scanning phase(s) of one or more of the plurality of irradiation spots is/are adjusted based at least in part on the determined speed of the microparticulate sample. The adjusted scanning frequency or phase(s) cause individual ones of the plurality of irradiation spot(s) to have different spatial phases with respect to an axis of the microparticulate sample along the flow direction. This is discussed below with reference to FIG. 3. Block 260 can be used in combination with, or independently of, block 250. Block 260 can be followed by block 220.

In some examples, an image flow cytometer includes a flow unit (e.g., flow system 128) configured to move the microparticulate sample through the flow chamber at a selected velocity. In some of these examples, block 260 can include adjusting the selected velocity based at least in part on spacing(s) of individual ones of the irradiation spots so that individual ones of the plurality of irradiation spot(s) have different spatial phases with respect to an axis of the microparticulate sample along the flow direction. This is also discussed below with reference to FIG. 2.

FIG. 3 shows an example of multi-scanning paths over a microparticulate sample 310. Traces 320 (solid), 330 (dashed), and 340 (dotted) show three respective irradiation paths over microparticulate sample 310. The paths may be traced by three separate irradiation spots, by one irradiation spot at three separate times (time-sequential scanning, e.g., with translation, block 140, between paths), or by any other combination of irradiation spot(s) and pass(es) over the microparticulate sample 310, e.g., three spots having centers or other reference points separated by ~20-30 µm parallel to axis F and scanning over a sample ~5-10 µm in diameter. Three traces are shown for illustration but the number of traces can be any number >2. Axis F is aligned with the flow direction. In this example, microparticulate sample 310 moves up in the figure (the direction of axis F) while the irradiation spots are scanned across microparticulate sample 310, so traces 320, 330, 340 travel down the figure. Example systems providing, e.g., depicted scanning patterns are shown in at least FIG. 4, 5, 7, 8, or 10.

In this example, the extent of microparticulate sample 310 on axis F is 0°-360° of spatial phase. The spatial phase of each trace 320, 330, 340 in this example is the coordinate along axis F where the trace first crosses axis F inside microparticulate sample 310. As shown, trace 320 has a phase of approximately 81°, trace 340 has a phase of approximately 51°, and trace 330 has a phase of approximately 21°. Since the traces have the same cycle period along axis F and are not in phase (separated by ≠0° of spatial phase, ≈30° in this example), each trace 320, 330, 340 can irradiate at least some portions of microparticulate sample 310 not irradiated by the others of traces 320, 330, 340. Accordingly, the measured data for each of traces 320, 330, 340 can be combined to produce an image of microparticulate sample 310 having higher resolution along axis F than can be provided by any individual trace. This can be performed as a stitching process, in some examples similar to television image deinterlacing. In some examples, a processing unit is adapted to provide an image of microparticulate sample 310 by aggregating the intensity signals (e.g., deinterlacing or otherwise grouping or arranging intensity signals from different traces together), by averaging the intensity signals (e.g., to reduce noise), by computing difference(s) between individual ones of the intensity signals, or any combination thereof.

In some examples, the 0° point or 360° point can alternatively be defined based at least in part on the boundaries of the cell intersecting with axis F, as marked by the diamonds in FIG. 3.

In some examples, adjustment(s) described above with reference to block 260, FIG. 2, alter the spatial phase of one or more trace(s), e.g., traces 320, 330, 340. In some examples, adjustment(s) described above with reference to block 260, FIG. 2, alter the spatial cycle length of one or more trace(s). In the example shown, each cycle of a trace 320, 330, 340 extends over roughly 90° on axis F. The processing unit (e.g., processor 186, FIG. 1) can adjust timing, phases, deflections, or other parameters such as those described above with reference to block 260, to scan multiple non-overlapping traces over the cell.

In some examples, signals from multiple spots can be combined to provide an image of a sample. For example, in systems using multiple spots such as discussed herein with reference to, e.g., FIGS. 1-16, images from a $-1^{st}$ order spot, a $0^{th}$ order spot, and a $+1^{st}$ order spot can be combined, e.g., to provide increased spatial resolution as in the example of FIG. 3. Additionally or alternatively, the images from the three spots can be averaged to reduce noise.

In various configurations described above, the shape of each microparticulate sample 310 can be obtained as a two-dimensional image. Accordingly, specific information such as the size (diameter) and shape (outline) of each microparticulate sample 310 can be obtained from the two-dimensional image. In an example, processor 186 forms the two-dimensional image by arranging a plurality of data values of the detected time-varying resultant-light intensity in a raster grid. Each data value is placed in a grid cell corresponding to the position of the irradiation spot when the data value was measured. Processor 186 then uses known object-detection algorithms, e.g., thresholding, edge detection (such as Laplace, Sobel, or difference-of-Gaussians), or flood-filling from a seed point, to detect the microparticulate samples 310 in the two-dimensional image.

Further, the classifications of samples to be observed, for example, the type of cells to be used as biological samples, can be discriminated based on size, shape, density, or polarization state of each microparticulate sample, without using a fluorescence spectral analysis. Some prior systems differentiate cell types using, e.g., fluorescent-dye conjugated antibodies. The fluorescent light emitted under laser illumination indicates the type of antibody, and thus the type of cell to which the antibody is bound. However, this requires that a sufficient number of antibodies bind to the cell to produce a detectable amount of fluorescent light. In contrast, in various aspects, cell type can be determined directly. This advantageously reduces the probability of mis-identification of cell type owing to insufficient binding of antibodies. It also permits discriminating between two cell types that have different shapes but that carry the same antigens and thus bind to the same antibodies. Some aspects use fluorescent-dyed antibodies or fluorescent probes (e.g., probe molecules) that bind to various components of the cell directly. Some such probes can bind e.g., to enzymes or other components of cells. Some probes use antibody labels and some probes bind without the use of antibodies.

Figure 4:
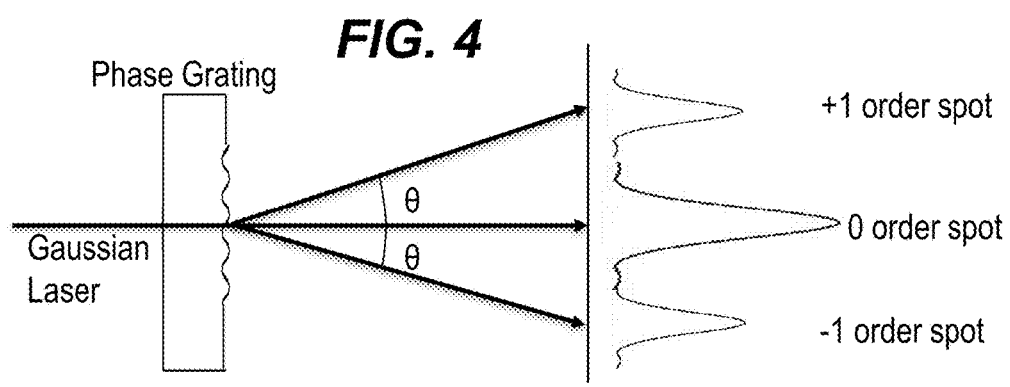
FIG. 4 shows an example optical configuration of an irradiation system.

FIG. 4 shows an example optical configuration in which a Gaussian-profile laser beam passes through a phase grating and is diffracted to produce at least three spots. The $\pm 1^{st}$ order spots are angularly displaced from the $0^{th}$ order spot by a diffraction angle $\theta = \lambda \times f_o$ (line pairs/mm). Therefore, the spot spacing d on the image plane is $d = \theta \times f$ (mm). In some examples, >95% efficiency is obtained for 3 spots, and an intensity ratio between the $0^{th}$ order spot and the $\pm 1^{st}$ order spots is 1:1-1:3.

FIG. 5 shows an example measurement system for detecting or measuring properties of microparticles. The particles are maintained in focus, e.g., in a hydrodynamically focused plane such as discussed below with reference to FIG. 9 or 11. In some examples, a consistent flow velocity is used; this can permit reproducing micro-particle images with accurate dimensions, as discussed herein with reference to, e.g., FIGS. 3 and 18.

In an example of conventional 3D laminar flow, flow speed varies radially outward from the center of the channel, e.g., as in the parabolic profile shown in FIG. 7. In an example of hydrodynamic focused planar flow (e.g., as in FIG. 9 or 11), the speed at which any particular particle moves is dependent on the distance from the lateral center of the flow. Therefore, some examples permit measuring individual particle flow speeds. Various examples permit measuring microscopic velocity in micro-fluidics channel.

Various aspects apply >1, e.g., 3 or >=3, spots scanning across flow direction and arranged to cross the flow channel in different areas arranged successively along the flow direction, as shown. Multiple spots can be obtained, e.g., by inserting a phase grating between a deflector and an objective lens. In the illustrated example, the deflector scans a laser beam in and out of the plane of the figure. Various examples herein use three spots, but this is not limiting.

Appropriate design of a phase grating can provide arbitrary intensity ratios between the +1, 0, −1 order diffracted spots. Some examples include substantially equal intensity or 0-order intensity 2-3 times higher than ±1-order spot. Distance between spots d can be $d = f$ (focal length)$\times \theta$ (diffraction angle), where $\theta = \lambda \times f_o$ (line pair/mm).

By aligning the 3 spots to flow direction, the 3 images provided by the respective spots can be used to determine changes over time. Knowledge of the distances between spots and determination of time differences between images can permit determining individual particle velocities. This can also permit "tracking," measuring the same particle multiple times. Cell tracking can permit, e.g., observing fast transition phenomena in live cells. In some examples, a particular particle (e.g., cell) can be tracked continuously using an X-Y deflector and synchronized displacement with flow velocity. In various examples, cell tracking permits performing observations on a specific cell both before and after activation of fluorescent probes that can reflect cellular activation states or presence of certain genes or enzyme molecules. Such probes can be activated, e.g., by a chemical introduced by bio-effective substance delivery system 906, FIG. 9.

FIG. 6 shows an example optical path 600. Microparticulate samples flow through a flow channel 602, which is irradiated by a laser (not shown). Resultant light passes through an objective 604, e.g., having NA=0.7. The light then passes through a lens arrangement 606, e.g., having f=12 mm and NA=0.16. The light then passes through a prism 608 having a 5 mm thickness and irradiates a photodetector 610, e.g., a split photodetector having one active area per spot (e.g., a three-way split for three spots). In the illustrated example, the spots are separated by ~35 μm in the flow channel and by ~126 μm at the plane of the photodiode.

In some examples of illumination at 405 nm, the following example gratings can provide 35 μm spacing of the −1, 0, and +1-order spots: 7.20 line pairs per millimeter (lpm) at a focal distance f=12 mm; 14.40 lpm at f=6 mm; 28.81 lpm at f=3 mm. The following example gratings can provide 50 μm spacing of the spots: 10.29 lpm, f=12 mm; 20.58 lpm, f=6 mm; 41.15 lpm; f=3 mm. In some examples, 8.63 lpm can be used. In a tested configuration, a diffraction angle of 3.0 mrad was measured, providing a 9.0 mm separation between the peaks of the +1 order spot and the −1 order spot at a distance of 1500 mm between the grating and the detector.

In some examples, the intensity ratio of the $0^{th}$ order to $\pm 1^{st}$ order is ~2:1, e.g., 2.0±0.4:1, and the total efficiency is >90%. In some examples, the grating has 7.20, 8.63, 14.40, or 28.81 line pairs/mm. The grating can include an antireflective coating (e.g., <0.5% reflection) on one or more surfaces. The grating can be made from or include, e.g., glass or quartz (n=1.47). The grating can have a thickness of, e.g., ~0.525 mm. The grating can have a size of, e.g., 10±0.1 mm on a side. The grating can have an effective area of, e.g., 7.0 mm on a side. The grating can be configured for an incident angle of 0±6°. The grating can have a Diffraction Efficiency >85%. The grating can be configured to provide a wavefront accuracy ≤15 mλ.

TABLE 1

|  | Power (mW) | % Efficiency | 0/±1 Ratio |
|---|---|---|---|
| 0 order | 4.38 | 45.0 | 2.1 |
| +1 order | 2.06 | 21.1 | 1 |
| −1 order | 2.05 | 21.0 | 1 |
| Total | 9.73 | 97.1 |  |

FIG. 6 shows an example beam path. The respective beam paths for multiple spots can substantially overlap. In an example, the spot separation is f×θ, resulting in θ=2.9 mrad for the illustrated configuration (spot separation=0.035 mm, f=12 mm). In some examples, the illustrated configuration provides a magnification of 3.6×.

FIG. 7 shows an example of velocity measurement using multiple-spot scanning.

In the illustrated example, particle velocity v=d/(t0−t+1)=d/Δt. In this example, a laminar flow is used so that particles move substantially parallel to the long axis of the flow chamber and the velocity of an individual particle is substantially constant between the +1-order spot and the −1-order spot. Distance d can be selected so that sample size<d<lens image height. The time resolution is limited by the scanning cycle time of the spots. Some examples include at least one of: illumination with wavelength λ=0.405 μm=405 nm, a focal length of f=12 mm, a grating of 20 line pair/mm, d=100 μm, or a scanning frequency of 1 MHz, corresponding to 1 μs resolution.

Figure 8:
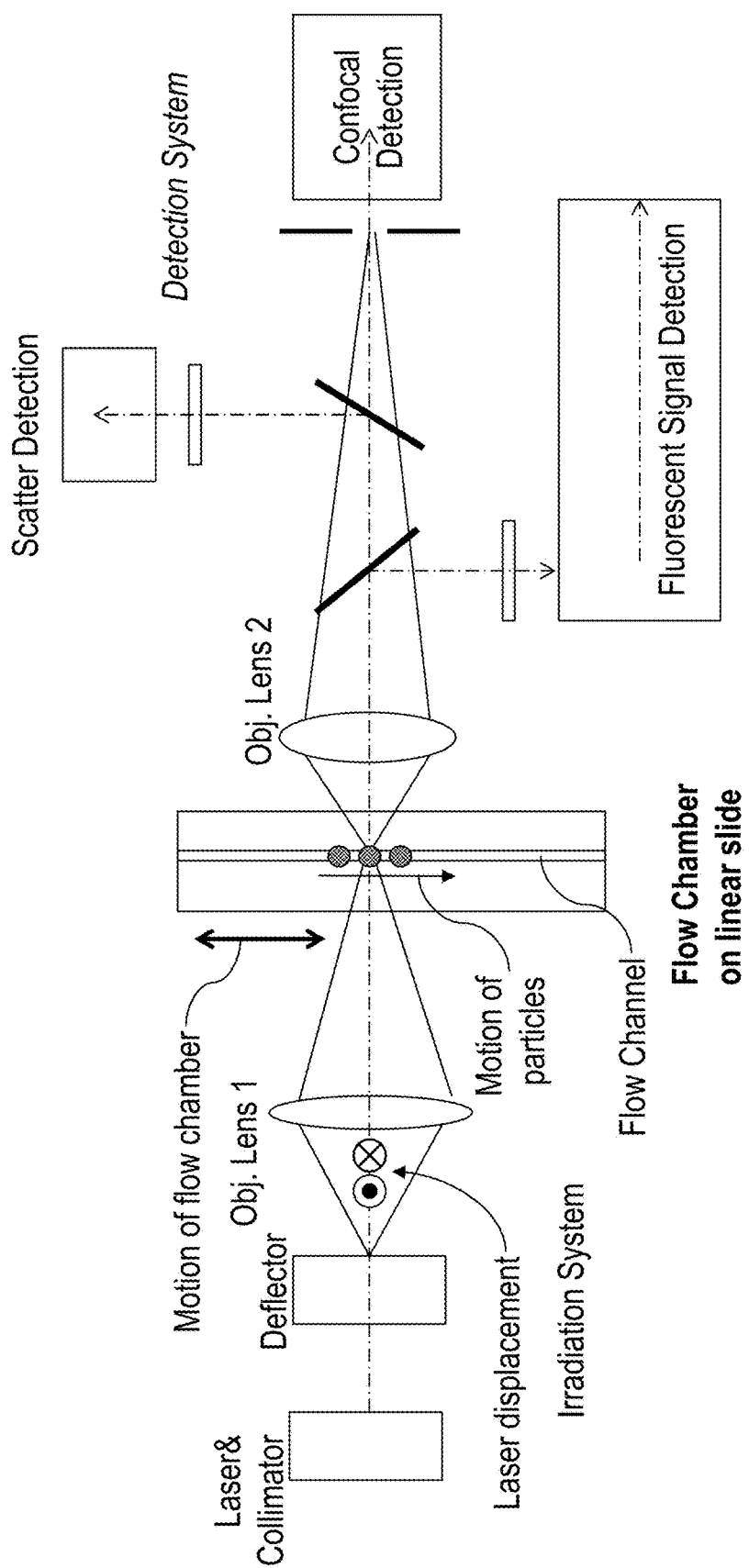
FIG. 8 shows an example system for cell tracking.

FIG. 8 shows an example system for cell tracking by, e.g., laser spot or flow-chamber displacement along the flow direction. The term "cell tracking" is used for explanation; cells or microparticulate samples other than cells can be tracked using "cell tracking" techniques described herein. Various examples of cell tracking include observing a particular cell at different time periods separated by Δt or n Δt. In the illustrated example, a micro-fluidics flow channel in the flow chamber is configured to provide stable laminar 2D flow, e.g., due to very small Reynolds number, over at least the distance between the laser spots. This can permit tracking particles, e.g., cells, by displacing the spots or the flow chamber along the flow direction.

In an example, 3 spot scanning with 100 μm distance between spots and a flow velocity of 0.1 m/s-1.0 m/s gives Δt=1 ms-0.1 ms. In some examples, the spots can be displaced over time along the flow direction.

In some examples, e.g., in which the field of the objective lens is limited, the flow chamber itself can be moved to permit tracking particles over a longer period of time than 2Δt as shown in FIG. 7. The flow chamber can be mounted on, e.g., a linear motor or one-axis stage. For example, with a 0.1 m/s-1.0 m/s flow speed, a 10 mm displacement can be performed by a slide, e.g., having a speed of 1.0 m/s. This can permit measuring a particular microparticle, e.g., every 0.1 s or less, e.g., every 10 ms (depending on flow speed).

In some examples using multiple irradiation spots, e.g., as in FIG. 4 or FIG. 8, the spots are not uniform in intensity. For example, a typical 3 spot intensity can be 1:2:1. Nonuniform irradiation can affect the detected signal intensities. In some examples, a processor 186 or other processing unit is adapted to adjust the detected intensity signals based on relative intensities of the plurality of irradiation spots and determine the image of the microparticulate sample based at least in part on the adjusted intensity signals. Some examples use white-level adjustment algorithms known in the television art.

FIG. 9 shows an example 900 of cell tracking in a flow chamber 902 using a laminar flow. In the illustrated example, the particles flow parallel to the channel wall. Shown is a hydrodynamic focusing unit 904 having a sample-fluid inlet carrying sample fluid that includes the particles. Two sheath-fluid inlets carry sheath fluid. The sheath fluid is brought into contact with the sample fluid in such a way as to focus the sample fluid flow, e.g., into a hydrodynamically planar flow or other laminar flow. Examples are discussed herein, e.g., with reference to FIGS. 17B-17C.

Four positions of a particle are shown, at times t=0, Δt, 2Δt, and 3Δt. The particle moves down the flow chamber 902 in the flow direction at flow speed v, e.g., 0.05 m/s-1.0 m/s. The flow chamber 902 itself moves opposite the flow direction ("chamber displacement") faster than flow speed v, e.g., at a speed of 1.05v-2.0v. In this example, the scanning and detection optics are fixed in position. Therefore, moving the flow chamber brings the particle back into position to be measured. The time difference Δt is determined by the relative speeds of the flow and the chamber. A particle can be measured at any number of times; times 0-3Δt are shown as nonlimiting examples.

In some examples, the optics move and the flow chamber 902 is fixed, or both the optics and the chamber move, or the optics include a scanner to move the position of irradiation opposite the flow direction, or any combination of any of those that provides relative motion between the irradiation position and the flow chamber. In various examples, the relative motion can be continuous or discrete. For example, the flow chamber can be moved in between measurements of a particle, and stationary during measurements of a particle. In various examples, an optical scanner, e.g., a galvo, can be used to redirect the irradiation to various points along the flow direction. Some of these examples can provide rapid translation, permitting measuring a particular cell or other microparticle more often. In various examples, a linear motor can move the flow chamber or at least some of the irradiation optics, e.g., up to 20 mm away from a home position. In some examples, In some examples, a bio-effective substance delivery system 906 is operationally arranged with respect to the flow chamber to selectively add a bio-effective substance, e.g., a drug or chemical, to the sample fluid. For example, after initial measurement(s) at t=0 or t=Δt, as shown, the bio-effective substance can be added. Subsequent measurements, e.g., at t=2Δt or 3Δt, can be used to determine effect(s) of the bio-effective substance on the microparticulate sample, e.g., a cell. Examples are discussed above, e.g., with reference to block 250.

In some examples, a cell or other microparticle can be continuously monitored while moving in a sample flow. For example, the irradiation location can be moved in the direction of the sample flow (+Y, in the illustrated example) and substantially at, e.g., the speed of the sample flow or the measured flow rate of a particular microparticle. This can permit an individual microparticle to be measured substantially continually over time. In some examples, the irradiation location can be moved in both ±X (across the flow) and ±Y (along the flow) directions to provide a 2-D scan of the cell (e.g., as in FIG. 3), over the course of time. The irradiation location can be moved by a single mechanism, e.g., translating the flow chamber at slightly more or slightly less than the flow speed to change the Y position of the irradiation spot with reference to the microparticulate sample over time. Alternatively, the irradiation chamber can be moved by two mechanisms, e.g., translating the flow chamber at the flow speed opposite the direction of the sample flow while rasterizing the irradiation spot in the XY plane. In some examples, multiple irradiation spots (e.g., FIG. 4-8, 10, 15, or 18-24C) can be used with any techniques described herein. Additionally or alternatively, multiple separate irradiation units can be used, e.g., multiple laser/lens/scanner arrangements, with respect to a single flow chamber.

FIG. 10 shows an example of microparticle measurement in which resultant light at each spot is measured by a respective optical detector, e.g., a photodiode or other configurations herein. Also shown are the detected signals for the example illustrated particles. In this example, each optical detector produces substantially the same signal, but shifted in time by Δt.

As discussed above with reference to FIG. 3, respective images of a microparticulate sample, e.g., a cell, from three spots can be combined. Techniques described above can additionally or alternatively be used with respect to images from multiple times, e.g., Δt and 2Δt. In some examples, images, e.g., from different spots or different times, can be compared to detect differences between the images. For example, comparing such images can be used to detect a change in a cell, e.g., formation or changes in size of a vacuole or other organelles in a cell. Comparing fluorescent images, as discussed below, can be used to detect changes in activity or viability of dyed cells or cell components.

In some examples, a single spot is used with relative motion between the irradiation location and the flow chamber, as discussed above. In some examples, multiple spots are used without relative motion between the irradiation location and the flow chamber. In some examples, multiple spots are used with relative motion between the irradiation location and the flow chamber.

FIG. 11 shows components of an example measurement system. The flow chamber is mounted on a linear motor driven by a linear motor controller to move the flow chamber opposite the flow direction between measurements, as discussed herein with reference to at least FIG. 10. After measurements of a particle or set of particles are complete, the linear motor controller can reset the flow chamber position, e.g., by moving the flow chamber in the direction of flow to a home position. Another particle or set of particles can then be measured. In some examples, closed-loop controllers can be used to control the linear motor.

Figure 12:
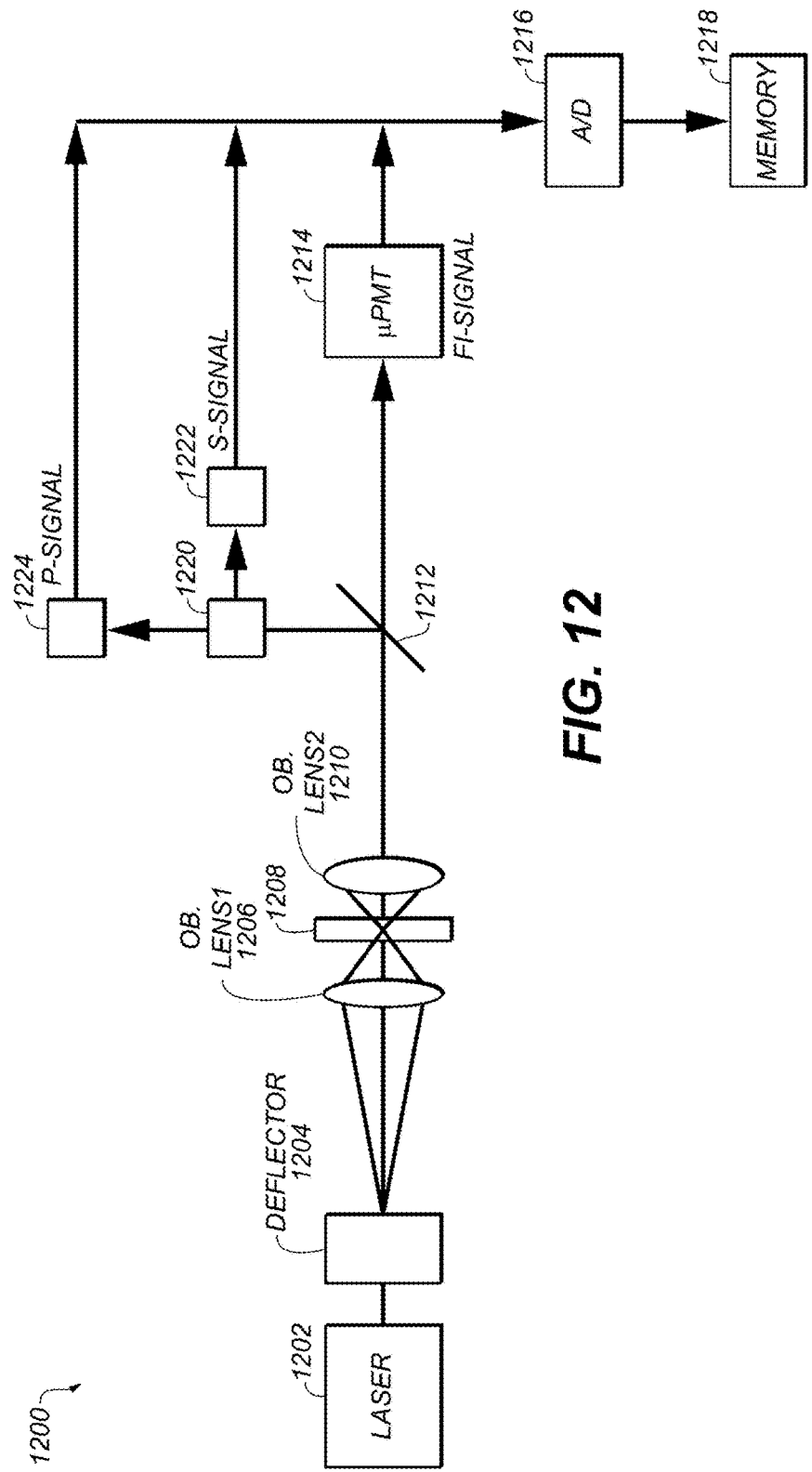
FIG. 12 shows an example system for measuring microparticles.

FIG. 12 shows an example system 1200 for measuring microparticles. Laser 1202 provides illumination, e.g., in UV, visible, or IR wavelengths. Deflector 1204 scans the illumination, e.g., as discussed herein with reference to FIG. 1, 3, 17E, 18, or 19. Lens 1206 focuses the illumination at irradiation location(s) in flow chamber 1208. Lens 1210 focuses resultant light. Although only a forward-scattering configuration is shown, reverse- or side-scatter lenses and detectors can additionally or alternatively be used.

Beamsplitter 1212, e.g., a wavelength-sensitive beamsplitter, reflects (or transmits) light substantially at the wavelength of the laser, transmits (or reflects) light, e.g., at selected fluorescence wavelength(s) or wavelength(s) substantially different from the wavelength of the laser, or any combination thereof. In the illustrated example, light transmitted by beamsplitter 1212 is measured by an optical detector 1214, e.g., a μPMT, which provides a fluorescence ("Fl") signal. Analog-to-digital (A/D) converter (ADC) 1216, e.g., a multichannel ADC or multiple single-channel ADCs, can provide digital representations of the signal from detector 1214 (or signals from detectors 1222, or 1224, below). Memory 1218, which can represent data storage system 140 or components thereof, can store digital representation(s) of respective signal(s) from respective detector(s).

Light reflected by beamsplitter 1212 passes to a polarizing beamsplitter 1220 that separates S- and P-polarized light. S-polarized optical detector 1222 provides an S-signal representing or associated with the S-polarized light, and P-polarized optical detector 1224 provides a P-signal representing or associated with the P-polarized light.

FIG. 13 shows an example measurement system 1300. Laser 1302 provides optical radiation, e.g., at λ=405 nm or other wavelengths. Mirror 1304 can have a high reflectivity at λ, e.g., 99.3%. Beamsplitter 1306, e.g., a polarizing beamsplitter ("PBS"), can be located, e.g., 65 mm from mirror 1304. Beamsplitter 1306 can reflect a small portion of the light striking the beamsplitter 1306, e.g., 1.7%, to a far-field focus sensing arrangement (omitted for brevity). The sensing arrangement can be used, e.g., for laser power monitoring. Lens 1308, e.g., located 40 mm from beamsplitter 1306, can have, e.g., a focal length of 40 mm. Lens 1308 can have a transmittance of 97.3%. Mirror 1310, e.g., located 55 mm from lens 1308, can direct the focused light. Polarizer 1312 and quarter-wave plate 1314, or other polarizing optics, can provide light of a desired polarization, e.g., linear or circular polarization, to grating 1316.

Grating 1316 can include a grating, e.g., as discussed herein with reference to FIG. 1, 4-8, or 12. Grating 1316 can provide multiple diffraction orders of the incident light. Objective 1318 can focus the incident light or diffraction orders thereof on a knife-edge 1320. Knife-edge 1320 can be used for testing the focus of the system, e.g., as in the examples discussed below with reference to FIGS. 14 and 15. In some examples, in place of knife-edge 1320, a flow channel 161 can be arranged. This can permit measuring microparticulate samples, e.g., as described herein. Objective 1322, e.g., a Nikon lens, can focus resultant light.

Chromatic beamsplitter 1324 can, e.g., separate light at the incident λ from other wavelengths, e.g., fluorescent or other wavelengths of resultant light. In some examples, chromatic beamsplitter 1324 can reflect, e.g., 96.1% of light at 405 nm, or transmit, e.g., 0.10% of light at 405 nm (or vice versa). S-polarized light 1326 can be focused by lens 1328 onto a photodetector 1330, e.g., an Si PIN photodiode. Photodetector 1330 can provide detection signals corresponding to, e.g., FS, SS, or transmitted light, or to non-fluorescence illumination.

FIG. 14 shows measurements of a focused spot clearing an optical knife edge made of a Cr mask. Measurements were taken using f=40 mm and a linear motor set to a velocity of 1 mm/s, so that a 1 ms time difference corresponds to 1 μm of distance. The measured rise of 1.29 ms corresponds to a spot size of 2.58 μm ($1/e^2$) or 1.51 μm (FWHM), with an effective NA=0.13.

FIG. 15 shows measured data of spot separation measured using the linear motor described with reference to FIG. 14. The design distance between spots was 35 μm. The measured distance from the $+1^{st}$-order spot to the $-1^{st}$-order spot distance is 70.9 μm, and from the $0^{th}$-order spot to the $+1^{st}$-order spot is 35.4 μm.

FIG. 16 shows portions of an optical detection system 1600. Component 1602 includes at least one barrel or lens that focuses incident light onto detector 1604, e.g., an optical detector such as a photodiode or other detectors herein. In the illustrated example, component 1602 includes two lenses mounted in a barrel. Dimensions A-G can be as in Table 2.

TABLE 2

| Label | Dimension |
|---|---|
| A | 4.003 mm |
| B | 9.68 mm |
| C | 8.5 mm diameter |
| D | 6.5 mm diameter |
| E | 0.5 mm |
| F | 5.5 mm |
| G | 9.18 mm |

In some examples, a three-spot image can be provided in transmission or two-pass reflection configurations. The beams for multiple spots can be deflected by a single deflector. Focus can be adjusted and deflection range can be measured.

In view of the foregoing, various aspects provide improved measurement of microparticulate samples. A technical effect is to capture data of constituents or sub-components of microparticulate samples. A technical effect is to capture data of microparticulate samples over time, e.g., to capture multiple images of a single or particular microparticulate sample over time. A further technical effect is to present a visual representation of images of microparticulate samples on an electronic display.

FIGS. 17A-17F show example flow-system configurations.

Figure 17A:
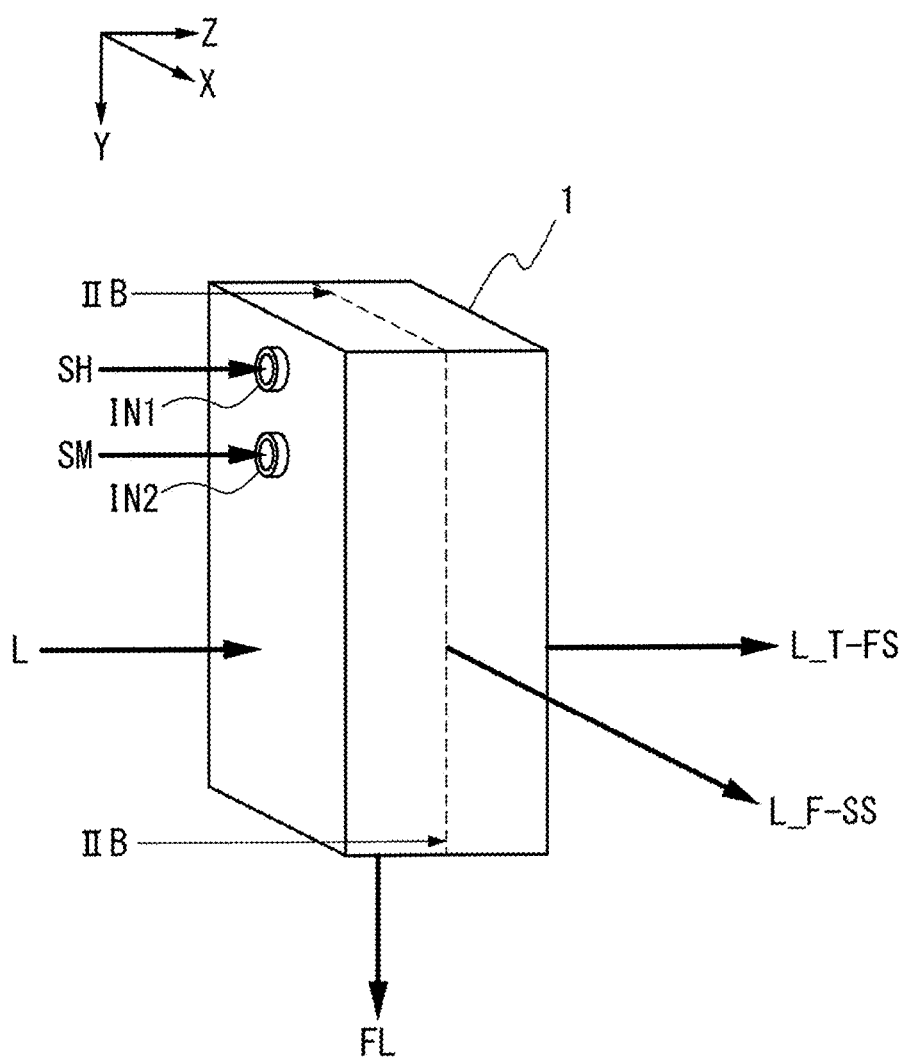
FIG. 17A is a perspective view schematically showing an exemplary configuration of a flow chamber.

FIG. 17A is a perspective view schematically showing an exemplary configuration of a flow chamber 1. A sheath flow SH flows into the flow chamber 1 from an inlet port IN1. For example, saline, which is an isotonic liquid, can be used as the sheath flow SH. However, the sheath flow SH is not limited to saline, but various types of liquid such as water, other aqueous solutions (whether isotonic or not), and organic solvents can be used.

Further, a sample flow SM including the microparticulate samples flows into the flow chamber 1 from an inlet port IN2. For example, saline, which is an isotonic liquid, can be used as the sample flow SM. However, the sample flow SM is not limited to saline, but various types of liquid such as water, other aqueous solutions (whether isotonic or not), and organic solvents can be used. The inflow pressure of the sample flow SM can be higher than the inflow pressure of the sheath flow SH.

The sheath flow SH and the sample flow SM merge in the flow chamber 1, so that a flow FL in which the sample flow SM is surrounded by the sheath flow SH is generated. The flow FL can be discharged to the outside of the flow chamber 1, for example.

Figure 17B:
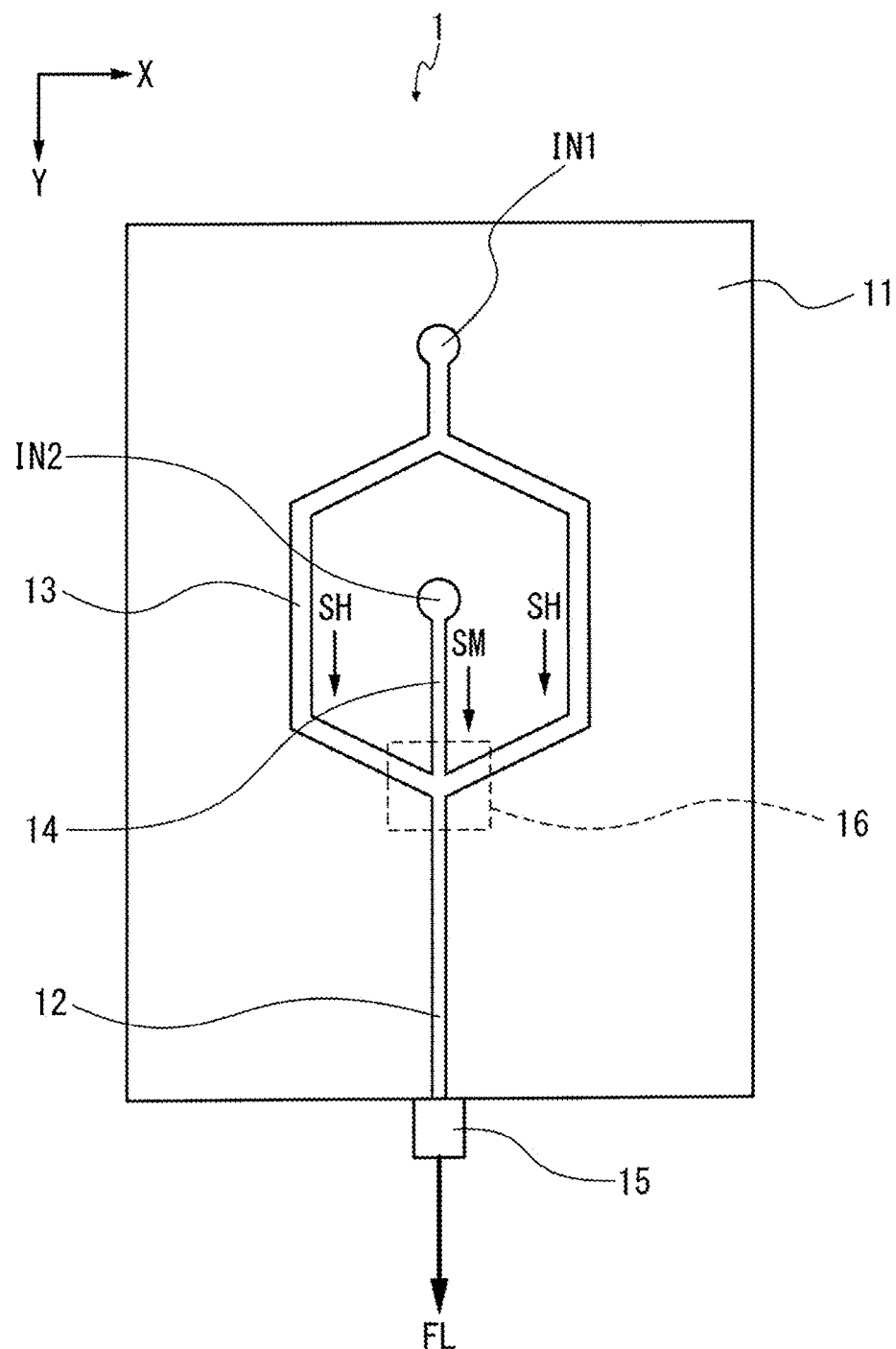
FIG. 17B is a sectional view schematically showing an exemplary sectional configuration of the flow chamber 1 in a plane taken along the line IIB-IIB of FIG. 17A.

FIG. 17B is a sectional view schematically showing an exemplary sectional configuration of the flow chamber 1 in a plane taken along the line IIB-IIB of FIG. 17A according to various aspects. Note that in FIG. 17B, a direction which is perpendicular to a Y-direction and parallel to the plane of the drawing is an X-direction. In the flow chamber 1, a micro flow channel 12, a flow channel 13, and a flow channel 14 are formed in a flat-plate-shaped member 11 through which laser light can be transmitted. The flow channel 13 is connected to the inlet port IN1 which is a pipe line that is bored in the surface of the flow chamber 1. Accordingly, the sheath flow SH flows through the flow channel 13. The flow channel 13 is branched into two channels, for example. The flow channel 14 is connected to the inlet port IN2 which is a pipe line that is, e.g., bored in the surface of the flow chamber 1. Accordingly, the sample flow SM flows through the flow channel 14. The flow channel 14 and the branched flow channels 13 merge and are connected with the micro flow channel 12. The micro flow channel 12 is a micro flow channel through which the microparticulate samples to be analyzed pass. The laser light L from the irradiation optical system is radiated onto the micro flow channel 12 in the direction from the front side of the plane of FIG. 17B toward the back side thereof, that is, in the direction perpendicular to the Y-direction. The orientations of components shown in this example are not limiting.

Figure 17C:
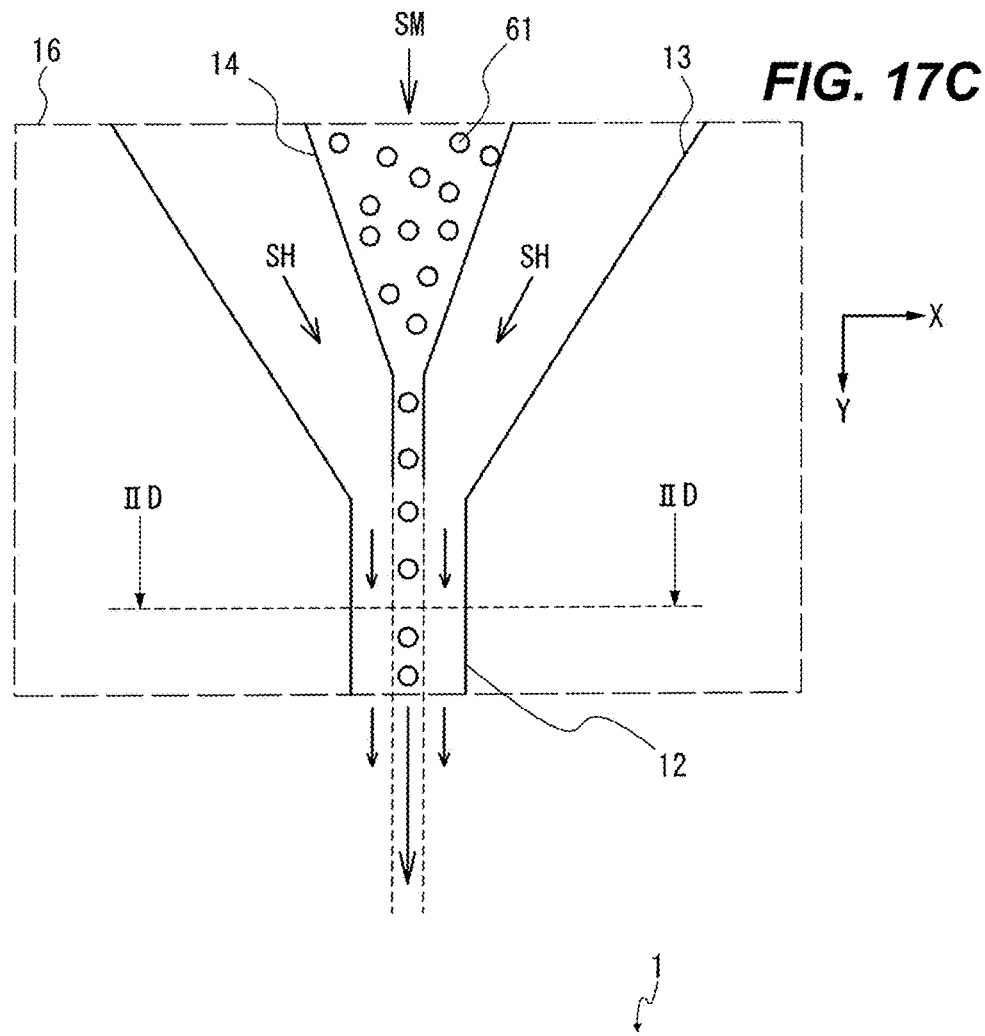
FIG. 17C is an enlarged sectional view schematically showing an exemplary confluent portion shown in FIG. 17B.

FIG. 17C is an enlarged sectional view schematically showing an exemplary confluent portion 16 shown in FIG. 17B according to various aspects. The sheath flow SH merges with the sample flow SM so as to enclose the sample flow SM. In this case, since the inflow pressure of the sample flow SM is higher than the inflow pressure of the sheath flow SH, microparticulate samples 61, which are randomly distributed, are aligned and flow in the sample flow SM within the micro flow channel 12.

Figure 17D:
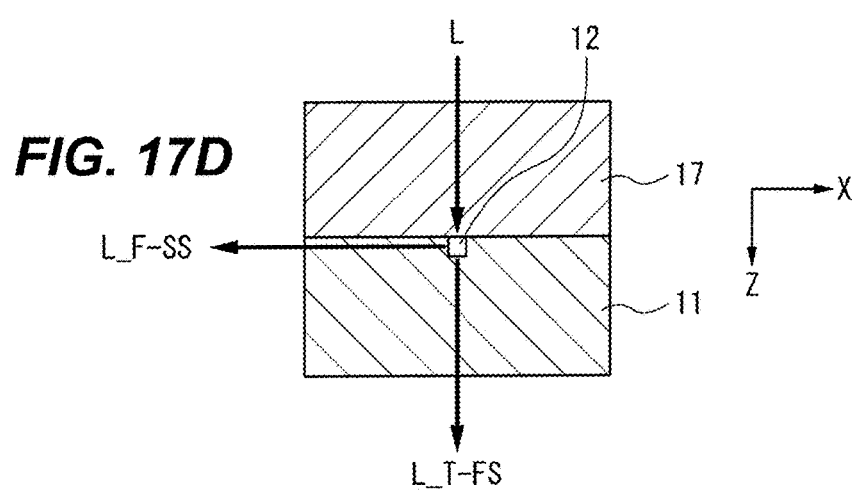
FIG. 17D is a sectional view schematically showing an exemplary sectional configuration of the flow chamber taken along the line IID-IID of FIG. 17C.

FIG. 17D is a sectional view schematically showing an exemplary sectional configuration of the flow chamber 1 taken along the line IID-IID of FIG. 17C according to various aspects. The micro flow channel 12 is formed as a groove in the flat-plate-shaped member 11. The flat-plate-shaped member 11 and the micro flow channel 12 are covered with a flat-plate-shaped member 17 through which laser light can be transmitted. In FIG. 17B, the laser light L from the irradiation optical system is incident on the upper surface of the flow chamber 1 from a Z-direction, which is a direction perpendicular to each of the X-direction and the Y-direction. The thickness in the Z-direction of each of the flat-plate-shaped member 11 and the flat-plate-shaped member 17 is 1 mm, for example. The flat-plate-shaped member 11 and the flat-plate-shaped member 17 are formed of a light transmissive material, such as resin, glass, or quartz, through which the laser light L can be transmitted.

In the flow cytometry, microparticulate samples to be analyzed are often cells of a living organism. Taking human blood as an example, examples of objects to be observed in the blood include erythrocytes (diameter of 7 to 8 thickness of about 2 µm), leucocytes (neutrophils: diameter of 12 to 15 acidocytes: diameter of 10 to 15 basophils: diameter of 10 to 15 lymphocytes: diameter of 6 to 15 monocytes: diameter of 20 to 30 µm), and blood platelets (diameter of 1 to 4 µm). The micro flow channel 12 is formed with dimensions that permit the microparticulate samples to be aligned in the Y-direction and move without overlapping each other within the flow channel. The micro flow channel 12 has a section size of the square of 50 for example, in the configuration shown in FIG. 17B.

Figure 17E:
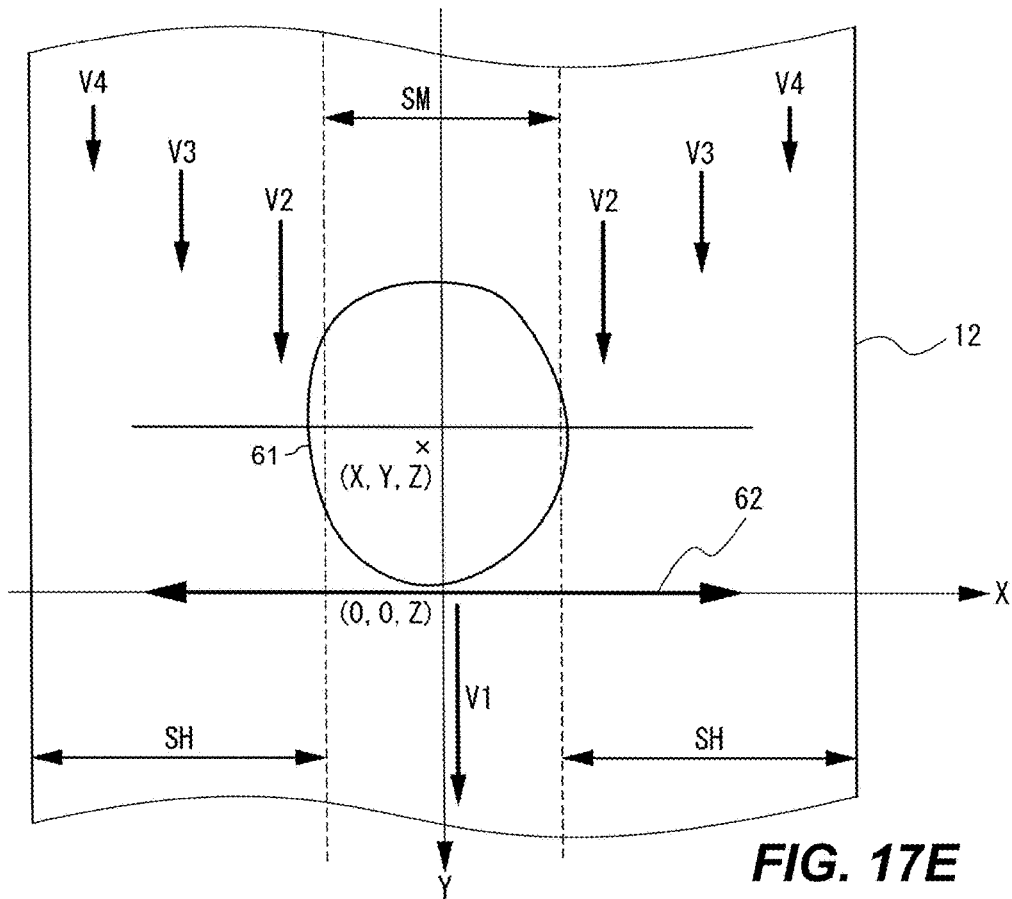
FIG. 17E is an enlarged front view showing a substantial part of a micro flow channel according to various aspects.
Figure 17F:
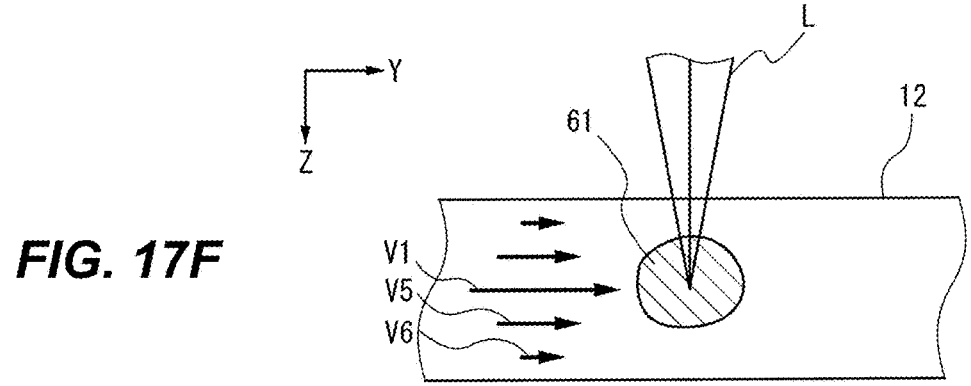
FIG. 17F is an enlarged sectional view showing the substantial part of the micro flow channel in an exemplary Y-Z section of FIG. 17E.

FIG. 17E is an enlarged front view showing a substantial part of a micro flow channel 12 according to various aspects. FIG. 17F is an enlarged sectional view showing the substantial part of the micro flow channel 12 in an exemplary Y-Z section of FIG. 17E. The flow rate of the liquid within the micro flow channel 12 shows such a parabolic change that the sample flow SM positioned at the center of the section (a flow rate V1 in FIGS. 17E and 17F) is fastest and the sheath flow SH becomes slower toward the wall surface of the micro flow channel 12 (V2 to V4 (V1>V2>V3>V4) in FIG. 17E) and V5 and V6 (V1>V5>V6) in FIG. 17F). As a result, the microparticulate samples 61 which move within the micro flow channel 12 move in the vicinity of the center of the section of the micro flow channel 12 so that the center-of-gravity position (X, Y, Z) is positioned substantially within the sample flow SM. Accordingly, even when the section size of the micro flow channel 12 is larger than that of each microparticulate sample 61, the plurality of microparticulate samples 61 can be aligned and move in a flow direction (Y-direction in FIGS. 17C and 17D) without overlapping with each other in the section of the micro flow channel 12.

Referring to FIGS. 17E and 17F, as shown, an irradiation optical system (e.g., FIG. 1) irradiates the microparticulate sample 61 (or other object) in the micro flow channel 12 with incident light L in an irradiation spot smaller than the microparticulate sample 61. As discussed herein, the irradiation optical system scans an irradiation position of the irradiation spot substantially in a direction X perpendicular to the flow direction Y. In doing so, the irradiation optical system scans the irradiation position through an irradiation volume, e.g., a volume the size of the irradiation spot swept along the path 62 shown in FIG. 17E. In various aspects, the micro flow channel 12 is shaped so that only one of the microparticulate sample 61 can be in the irradiation volume at one time. This advantageously provides measurement of the microparticulate sample 61 without concern for "coincidences," events in which two (or more) microparticulate samples 61 are erroneously detected as one microparticulate sample 61.

Figure 18:
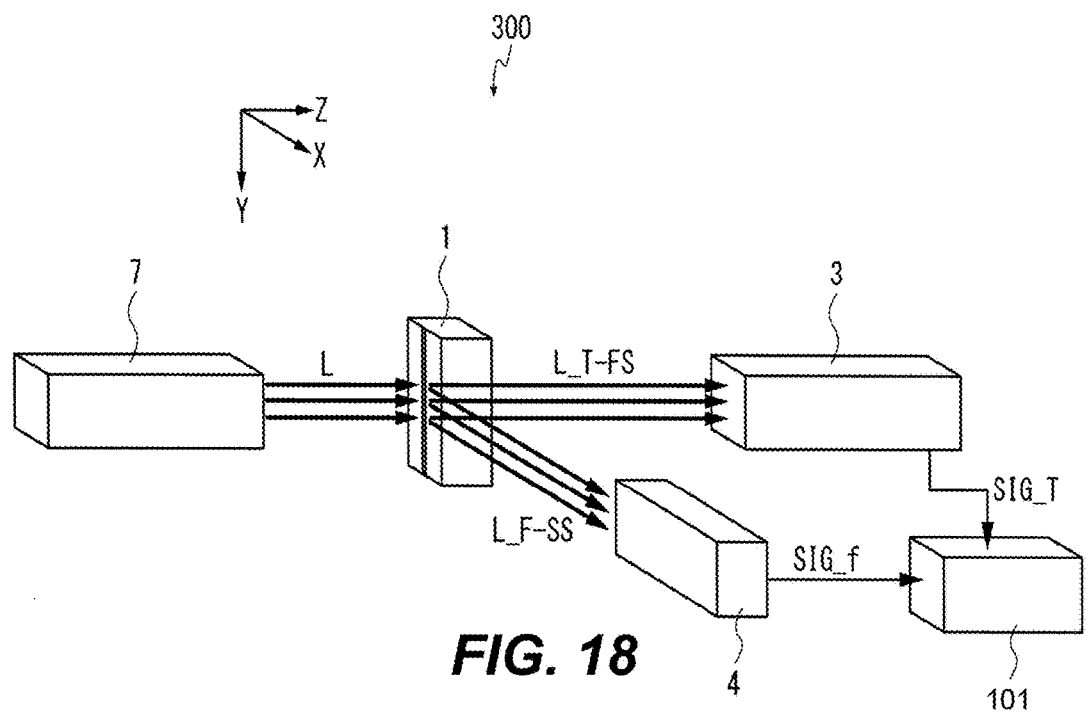
FIG. 18 is a configuration diagram showing a schematic configuration of an image flow cytometer 300 according to an example embodiment.

FIG. 18 is a configuration diagram showing a schematic configuration of an image flow cytometer 300 according to an example embodiment. The image flow cytometer 300 has a configuration including an irradiation optical system 7, FIG. 11. A data-processing system 101 can implement a control unit. The data-processing system 101, e.g., including a processor 186, can receive transmitted-resultant-light data (SIG_T) from detection optical system 3 and fluorescent- or side-scattered-resultant-light data (SIG_f) from detection optical system 4. Examples of irradiation optical systems and detection optical systems are described herein, e.g., with reference to FIGS. 1, 3-13, and 16. The illustrated example shows three spots, but a single spot or any number of spots can be used with components herein.

In various aspects, the flow velocity, spot size, and X-axis deflection frequency parameters are set to (1) provide an excitation intensity level of a fluorescent dye marker in a desired area of the microparticulate sample above a threshold; and (2) provide a desired resolution, bit depth, and precision of the scan image. In various aspects, the spot size is selected, then flow velocity and scan frequency are controlled. An example is a spot with a FWHM diameter of 2 µm, a deflection frequency of 1 MHz, and a flow rate of 1 m/s. This example provides 1 µm scan vertical resolution with >½ intensity of a Gaussian spot profile. A 2 µm FWHM advantageously permits measuring data from 10 µm particles such as blood cells with effective focal depth. In another example, the spot size is 0.5 µm, which provides higher resolution. The flow speed can be ¼ m/s, or the scan frequency can be 4 MHz, or a combination. Generally, flow speed can be reduced or scan frequency can be increased by the same ratio as the spot size is decreased, or vice versa (increase spot size and increase flow speed or decrease scan frequency). Flow speed can be selected to balance desired resolution and throughput. Faster flow speed provides higher throughput and lower vertical resolution. Slower flow speed improves vertical image resolution with lower throughput. The horizontal resolution is determined by the scanning frequency and sampling frequency (e.g., number of samples per scan). These parameters can be selected to advantageously permit measuring absolute particle size and shape. Prior flow cytometers do not provide the ability to make such measurements.

In the image flow cytometer 300, a deflector scans the laser light, i.e., moves the irradiation location, in an X-direction. The deflector may also scan the light in a Y direction, different from e.g., substantially perpendicular to, the X-direction. In this example, the Y-direction is the direction of flow of fluid in the micro flow channel 12. The frequency for laser scanning can be, e.g., 1 MHz. In an example, when the flow rate of the microparticulate samples is 1 m/s, the laser light completes one cycle in the X-direction (across the microparticulate sample and back) while the microparticulate samples move by 1 µm in the Y-direction. FIG. 3, traces 320, 330, and 340, show effects of scanning the irradiation location in the X-direction while moving the microparticulate sample 310 in the Y-direction. The irradiation location is rasterized over the microparticulate sample 310 to successively and individually irradiate many points or structures within the microparticulate sample 310. Various aspects advantageously provide particle flows with constant velocity on the Y-axis. Therefore, with only X-axis scanning, a two-dimensional image can be produced. This is unlike laser scanning confocal microscopes (e.g., the ZEISS LSM 710), in which a stationary sample is rasterized with a two-axis scanning device such as an X-Y galvanomirror. Two-axis scanners require significantly more moving parts and are more mechanically complex than one-axis scanners. Using a one-axis scanner advantageously permits simpler, more reliable construction. Additionally, using a flow permits measuring large numbers of microparticulate samples 310 in quick succession. Laser-scanning confocal microscopes require samples to be prepared, e.g., on slides, and the focal point of the microscope to be moved to focus on the samples. Various aspects described herein do not require these steps, and produce two-dimensional data without them.

For example, when the microparticulate samples are neutrophils (diameter of 12 to 15 µm), which are one kind of leucocytes, the neutrophils can be scanned at about 12 to 15 X-direction cycles per microparticulate sample 310. In this case, in the about 12 to 15 cycles during which the neutrophils are scanned, the light intensity of the transmitted light and the light intensity of the forward-scattered light vary. For example, when the irradiation spot of the laser light is located on or within a neutrophil, the intensity of the laser light decreases and the intensity of the forward-scattered light increases due to reflection, scattering, absorption, or the like by the neutrophil. On the other hand, when the irradiation spot of the laser light deviates from (does not irradiate) any neutrophil, the laser light is not reflected, scattered, and absorbed by a neutrophil, so that the intensity of the transmitted light increases and the intensity of the forward-scattered light decreases compared to when the irradiation spot is located on or within a neutrophil.

In various aspects, control unit 5 processes signals from the detection optical systems 3 and 4 to determine properties of features within a microparticulate sample or other object. For example, individual mitochondria within a cell can be located using fluorescent tagging of mitochondria, e.g., with LIFE TECHNOLOGIES MITOSOX red mitochondrial superoxide indicator. As the irradiation spot is scanned over a cell that has been dyed with MITOSOX, red fluorescence will be detected when the irradiation spot is over a live mitochondrion. In this way, positions, counts, and distributions of mitochondria in a cell can be determined. In another example, dyes such as DHR 123 can be used similarly for detecting mitochondria.

Internal structures of other objects can also be determined. For example, any internal structure such as a labeled nucleus can be identified and distinguished from surrounding organelles. Other organelles can also be identified. In another example, in-situ hybridization problems can be clearly identified, as can mRNA. RNA transcripts can be identified by different fluorescent probes.

Figure 19:
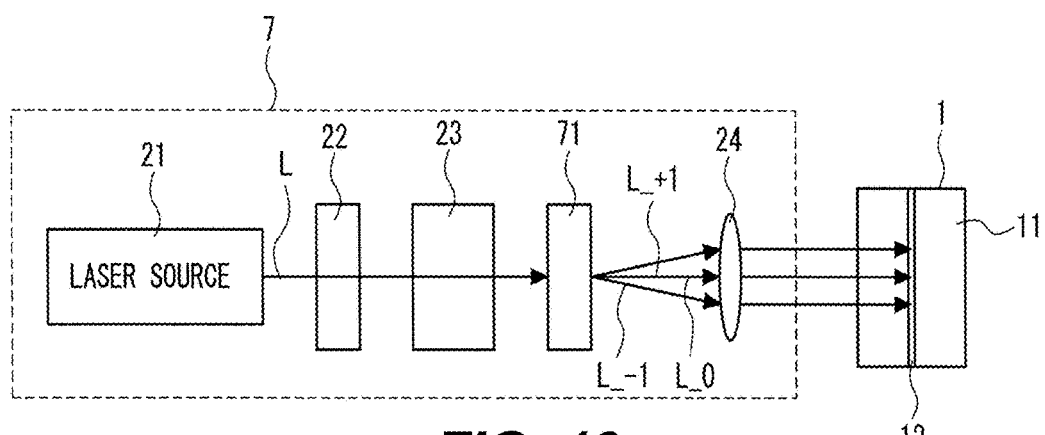
FIG. 19 is a block diagram schematically showing a configuration of an exemplary irradiation optical system.

FIG. 19 is a block diagram schematically showing a configuration of an exemplary irradiation optical system 7. The irradiation optical system 7 has a configuration in which a diffraction grating, e.g., phase diffraction grating 71, is added to the irradiation optical system 2. The phase diffraction grating 71 is disposed between the deflector 23 and the objective lens 24. The laser light L is diffracted by the phase diffraction grating 71, so that zero-order diffracted light $L\_0$, plus-first-order diffracted light $L\_+1$, and minus-first-order diffracted light $L\_1$ are generated. The objective lens 24 is designed to cause the zero-order diffracted light $L\_0$, the plus-first-order diffracted light $L\_+1$, and the minus-first-order diffracted light $L\_1$ to converge to the diffraction limit at different positions in the Y-direction (shown in FIG. 18) of the micro flow channel 12 of the flow chamber 1.

In various configurations, when the laser light L is diffracted by the phase diffraction grating 71, the diffracted light having an order greater than ±1 is generated. However, the diffracted light having a large order has a large diffraction angle, which may cause a situation in which the diffracted light is not incident on the objective lens 24, or the focal point position is liable to deviate from the micro flow channel 12 even when the diffracted light is incident on the objective lens 24. Further, the diffracted light having a large order has a small light intensity. An exemplary phase grating can provide over 90% of the incident intensity within the first-order, so higher-order spots can have negligible intensity. Accordingly, various examples herein assume that the diffracted light having an order greater than ±1 is not used for detection. However, this does not preclude the use of the diffracted light having an order greater than ±1 for detection. Such light can be used by suitably configuring the objective lens 24, or by adding other components such as mirrors to direct the ±2 order and above. In various aspects, only positive order(s), or only negative order(s), of diffracted light are used with the zero-order light (e.g., 0 and +1 or 0 and 1).

The zero-order diffracted light L_0, the plus-first-order diffracted light L_+1, and the minus-first-order diffracted light L_1 are focused at different positions spaced apart from each other in the Y-direction in the micro flow channel 12. As in the first exemplary embodiment, transmitted light, forward-scattered light, fluorescence, and side-scattered light are generated from each of the zero-order diffracted light L_0, the plus-first-order diffracted light L_+1, and the minus-first-order diffracted light L_1 which are focused in the micro flow channel 12.

Figure 20:
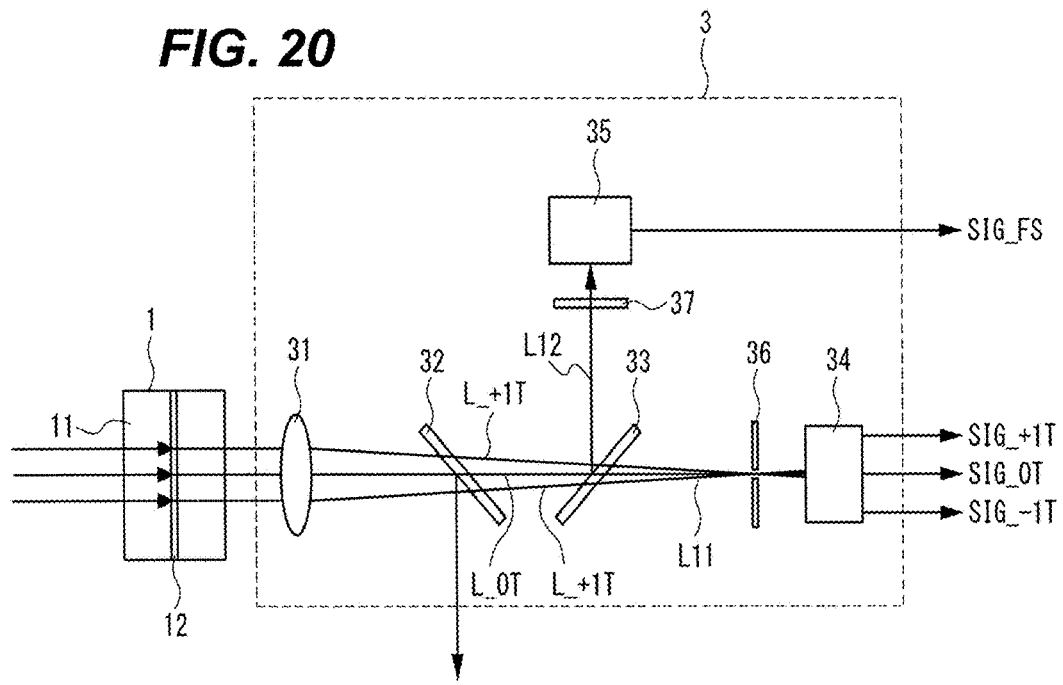
FIG. 20 is a configuration diagram schematically showing an exemplary configuration of a detection optical system of an image flow cytometer.

FIG. 20 is a configuration diagram schematically showing an exemplary configuration of the detection optical system 3 of the image flow cytometer 300. The transmitted light of the zero-order diffracted light L_0 is transmitted light L_0T. The transmitted light of the plus-first-order diffracted light L_+1 is transmitted light L_+1T. The transmitted light of the minus-first-order diffracted light L_1 is transmitted light L_1T. FIG. 20 is a configuration diagram schematically showing an exemplary configuration of the detection optical system 3 of the image flow cytometer 300. The objective lens 31 of the detection optical system 3 is arranged to cause the transmitted light L_0T of the zero-order diffracted light, the transmitted light L_+1T of the first-order diffracted light, and the transmitted light L_1T of the minus-first-order diffracted light to form an image at different positions on the receiving surface of the photodetector 34. Accordingly, the photodetector 34 can receive, in a distinguishable manner, the transmitted light L_0T of the zero-order diffracted light, the transmitted light L_+1T of the first-order diffracted light, and the transmitted light L_1T of the minus-first-order diffracted light. The photodetector 34 outputs, to the processor 186, signal SIG_0T representing the transmitted light L_0T of the zero-order diffracted light, signal SIG_+1T representing the transmitted light L_+1T of the first-order diffracted light, and signal SIG_1T representing the transmitted light L_1T of the minus-first-order diffracted light.

Figure 21:
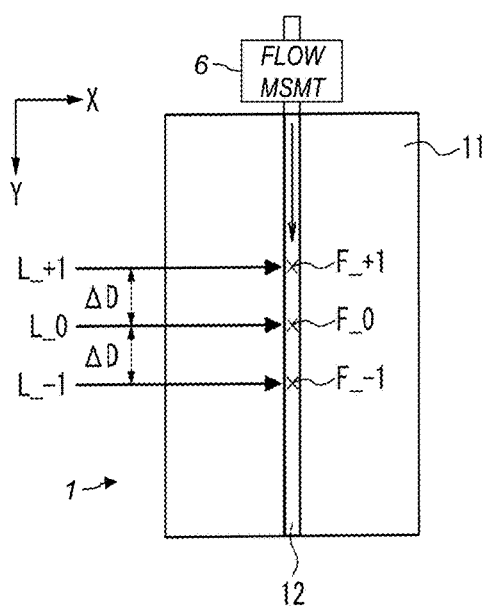
FIG. 21 is an enlarged view showing the vicinity of a micro flow channel of an image flow cytometer according to various aspects.

FIG. 21 is an enlarged view showing the vicinity of the micro flow channel 12 of the image flow cytometer 300 according to various aspects. In the micro flow channel 12 of the image flow cytometer 300, the microparticulate samples 61 sequentially pass through a focal position F_+1 of the plus-first-order diffracted light L_+1, a focal position F_0 of the zero-order diffracted light L_0, and a focal position F_1 of the minus-first-order diffracted light L_1, in the stated order. The focal positions are marked with "X" signs to indicate that, in this view, laser light L (FIG. 18) is passing from in front of the plane of the figure to behind the plane of the figure.

This enables the processor 186 to observe a sequential change of a signal SIG_+1T, a detection signal SIG_0T, and a signal SIG_1T. The distances between the focal point position F_+1 of the plus-first-order diffracted light L_+1, the focal point position F_0 of the zero-order diffracted light L_0, and the focal position F_1 of the minus-first-order diffracted light L_1 are known values uniquely determined from the layout of the phase diffraction grating 71, the objective lens 24, and the micro flow channel 12; the grating pitch of the phase diffraction grating 71; and the NA (numerical aperture) of the objective lens 24. In an example, the distance between the focal position F_+1 of the plus-first-order diffracted light L_+1 and the focal position F_0 of the zero-order diffracted light L_0 is $\Delta D$. Similarly, the distance between the focal position F_0 of the zero-order diffracted light L_0 and the focal position F_1 of the minus-first-order diffracted light L_1 is $\Delta D$. In an example, $\Delta D$ is 25-50 µm.

In an example, laser light L is diffraction-limited and the objective lens 24 has a numerical aperture (NA) of 0.15 and a focal length of 20 mm. The spot separation $\Delta D = 20$ µm at 1 m/s sample flow. All samples can be detected for up to 25,000 cells/sec. The time between spots is ~20 µs or ~40 µs.

In various aspects, higher resolution is achieved by stitching, e.g., three images. This can improve the scan resolution from 1 µm to 0.3 µm.

In another example, NA=0.75. The ±1st order light beams have an angle of 30° with the object to be tested. This permits determining a 3-D image or structure of the object. In this and other examples, the 3-D image can be represented as a voxel array, as polygons, or in other representations. Objects to be tested can be of various sizes.

FIG. 21 also shows an example in which the flow rate measurement device 6 is provided as an example of flow rate measurement means. In other examples, the phase diffraction grating 71, FIG. 19, and the processor 186 collaborate with each other to obtain the flow rate Vf of the microparticulate samples within the micro flow channel 12. Accordingly, in this exemplary embodiment, it can also be understood that the phase diffraction grating 71 and the processor 186 constitute a flow rate measurement device. A flow rate measurement device 6 can also be used in combination with the phase diffraction grating 71 and the processor 186, e.g., to reduce noise in determinations of Vf.

Figure 22:
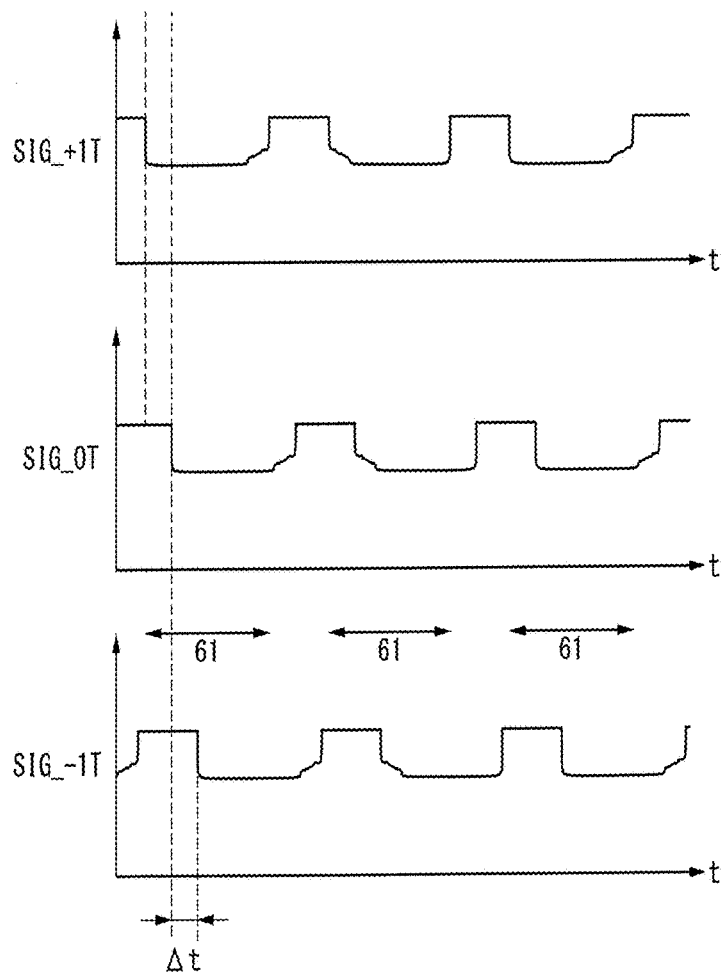
FIG. 22 is a timing diagram showing a variation of each of a detection signal SIG_+1T, a detection signal SIG_0T, and a detection signal SIG_−1T, according to an example.

FIG. 22 is a timing diagram showing a variation of each of a detection signal SIG_+1T, a detection signal SIG_0T, and a detection signal SIG_−1T, according to an example. In this case, the processor 186 can observe a time interval $\Delta t$ between changes of the detection signal SIG_+1T, the detection signal SIG_0T, and the detection signal SIG_1T. Accordingly, the processor 186 can calculate the flow rate Vf of the microparticulate samples within the micro flow channel 12 based on the distance $\Delta D$ and the time interval $\Delta t$: $Vf = \Delta D / \Delta t$. Thus, the processor 186 performs arithmetic processing using the flow rate Vf in the same manner as in the second exemplary embodiment, thereby making it possible to generate a two-dimensional image of each microparticulate sample.

In this configuration, the processor 186 can monitor the flow rate Vf within the micro flow channel 12 in real time. This enables the processor 186 to generate a two-dimensional image of each microparticulate sample while reflecting the variation of the flow rate Vf. Thus, according to this configuration, as compared with the first exemplary embodiment, a distortion of a two-dimensional image to be generated can be reduced even when the flow rate Vf varies. Therefore, according to this configuration, it is possible to obtain a two-dimensional image of each microparticulate sample with high accuracy.

This exemplary embodiment illustrates the case where the plus-first-order diffracted light L_+1, the zero-order diffracted light L_0, and the minus-first-order diffracted light L_1 are incident on the micro flow channel 12 in parallel. However, the plus-first-order diffracted light L_+1, the zero-order diffracted light L_0, and the minus-first-order diffracted light L_1 can also be made incident on the same position by designing objective lens 24 to cause those orders of light to converge.

Figure 23:
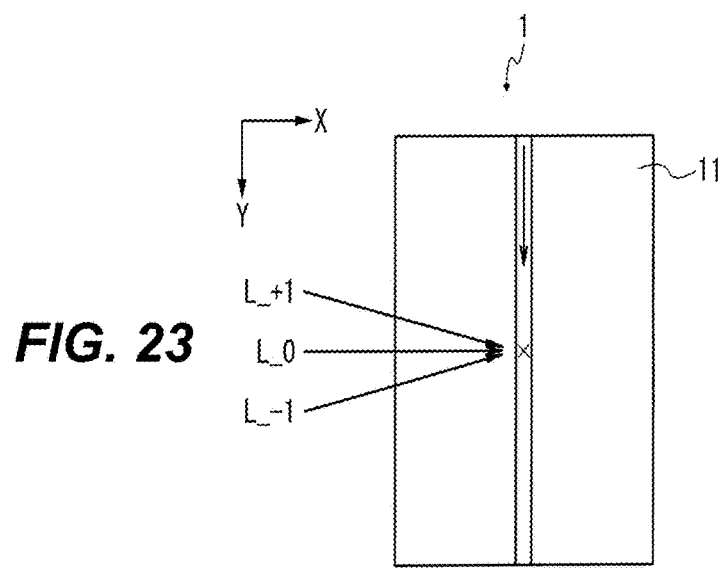
FIG. 23 is an enlarged view showing the vicinity of a micro flow channel in an example in which a plus-first-order diffracted light L_+1, a zero-order diffracted light L_0, and a minus-first-order diffracted light L_−1 are made incident on the same position.

FIG. 23 is an enlarged view showing the vicinity of the micro flow channel 12 in an example in which a plus-first-order diffracted light L_+1, a zero-order diffracted light L_0, and a minus-first-order diffracted light L_−1 are made incident on the same position, which is marked with an "X". In this case, the flow rate Vf is not calculated as described above with reference to FIG. 22. Vf can be determined, e.g., using a flow rate measurement device 6. The flow rate measuring device 6 can be disposed in the micro flow channel 12 of the flow chamber 1 or in another flow channel connected to the micro flow channel 12, and can measure the flow rate of microparticulate samples or liquid within the micro flow channel 12. In this case, a flow rate in the vicinity of the center of the micro flow channel 12 (that is, a peak value of the flow rate within the micro flow channel 12 in a certain section), for example, can be measured. The flow rate measuring device 6 outputs a flow rate signal SIG_V, which represents the measured flow rate, to the processor 186.

In this example, the microparticulate samples can be irradiated with light from three different directions at the same time. Accordingly, the transmitted light, the scattered light, the fluorescence, and the like include information obtained from the light incident from three different directions. The processor 186 can also analyze a three-dimensional structure of each microparticulate sample by appropriately processing the information obtained from the light incident from three different directions by means of a three-dimensional parallax. Light can also be directed from multiple directions onto a common position "X", e.g., from multiple lasers or light sources, or multiple optical fibers carrying light from a common light source to different positions with respect to the common position.

Figure 24A:
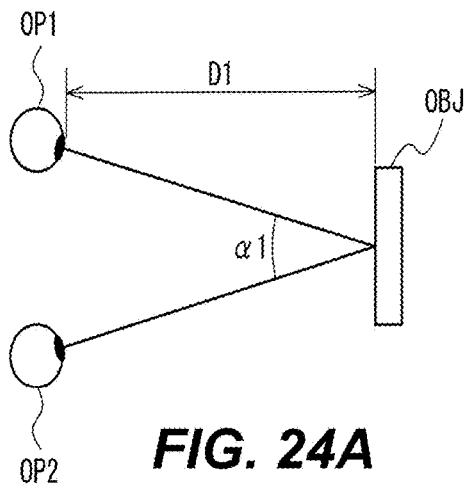
FIG. 24A is a view showing an example of parallax when a distance is long between an observation points and an observation object.
Figure 24B:
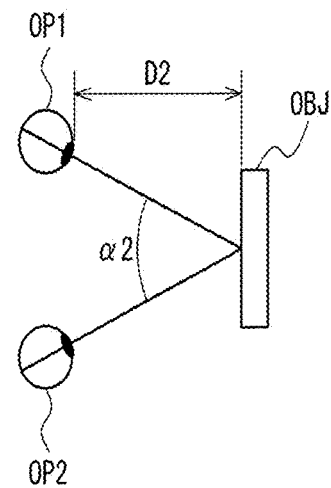
FIG. 24B is a view showing an example of parallax when a distance is short between the observation points and the observation object.
Figure 24C:
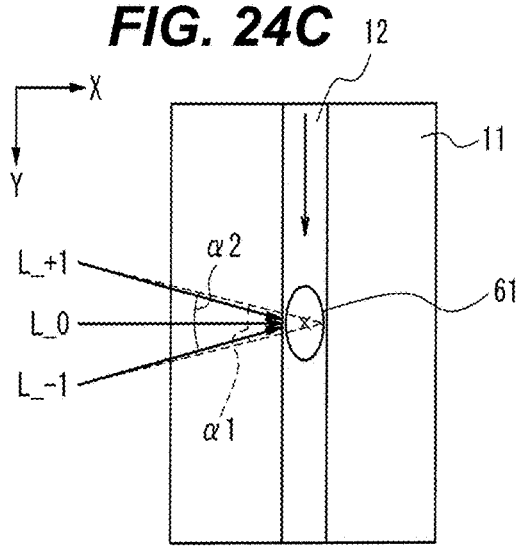
FIG. 24C is an enlarged view of a vicinity of the micro flow channel 12 showing three-dimensional parallax according to various aspects.

FIGS. 24A-24C show examples of three-dimensional parallax.

FIG. 24A is a view showing an example of parallax when a distance is long between an observation points and an observation object. Shown in FIG. 24A, when a distance between the observation points OP1 and OP2, and the observed object OBJ, is D1, a parallax angle is α1.

FIG. 24B is a view showing an example of parallax when a distance is short between the observation points and the observation object. Shown in FIG. 24B, when the horizontal distance between the observation points OP1 and OP2, and the observed object OBJ is D2, a parallax angle is α2. When D1 is greater than D2 (D1>D2), α1 is less than α2 (α1<α2).

FIG. 24C is an enlarged view of a vicinity of the micro flow channel 12 showing the three-dimensional parallax according to various aspects. In FIG. 24C, the microparticulate sample 61 corresponds to the observed object OBJ of FIGS. 24A, 24B. In FIG. 24C, D1 is a distance between the observation points OP1 and OP2 and the backside of the microparticulate sample 61. D2 is a distance between the observation points OP1 and OP2 and the front side of microparticulate sample 61. In this case, the three-dimensional parallax Δα can be expressed as Δα=α2−α1. Therefore, three-dimensional data such as the steric configuration of the microparticulate sample 61 can be obtained by measuring Δα. There are many ways to create 3D images. In this example, two images with different Δα values are obtained by independently detecting signals of L_+1 and L_1. This is similar to the way to consumer 3D televisions provide a 3D image. In various aspects, two 2-D scans can be combined to provide a 3-D dataset. Scans can be taken in the X-Y and X-Z planes.

Parallax affects the view of moving microparticulate samples 61 or other objects. For a certain distance the object moves, features of the object closer to the viewer move through a wider angular range than features farther from the viewer. This is indicated by FIGS. 24A and 24B, which show that the distance between the viewer's eyes subtends a larger angle α2 if the object is close than the angle α1 if the object is farther away. Referring back to FIG. 24C, features of the microparticulate sample 61 (e.g., mitochondria in a cell) are in different positions in the L_+1 image than in the L_1 image. The closer the feature is to the irradiation optical system 7, the more different the positions will be in the two images. Therefore, the processor 186 can locate common features in the L_+1, L_0, and L_1 images (or any combination of those or any number of images at different angles). The controller can compare the positions of the corresponding features in the three images and use geometric and trigonometric relationships to infer the 3-D positions of those features within the microparticulate object 61. Features can include organelles, inclusions, defined portions of a cell membrane, or other objects smaller than, or contained within, the microparticulate sample 61.

Some example configurations herein, e.g., in FIGS. 1-5 and 7-12, can be used with flow cells, pumps, cytometers, lasers, irradiation systems, detection systems, and other components described and shown in FIGS. 4-24. For example, irradiation and detection systems such as those discussed with reference to FIGS. 17A-24C can be used in place of or in addition to irradiation and detection systems shown in FIG. 1 and FIGS. 7,9-11. Flow chambers such as those discussed with reference to FIGS. 17A-24C can be used in place of or in addition to flow chambers shown in FIG. 1,5, or 8-11.

Some example configurations include both multiscanning and relative motion of the irradiation spots and the flow chamber 160. For example, a flow cytometer can include a stage to translate the flow chamber 160 and a grating to provide three irradiation spots from a single laser. These configurations can provide higher-resolution imagery, e.g., of multiple microparticulate samples concurrently flowing through a flow chamber, and can provide such imagery over time to observe, e.g., effects of bio-effective substance(s). In some of these example configurations, the flow chamber provides a hydrodynamically planar flow.

EXAMPLE CLAUSES

A: An image flow cytometer for observing a microparticulate sample, the flow cytometer comprising: a flow chamber including a flow channel formed therein to permit the microparticulate sample to travel in a flow direction along the flow channel; an irradiation system adapted to scan an irradiation spot across a sensing area of the flow channel in a scan direction different from the flow direction; a detection system that detects a time-varying intensity of resultant light from the sensing area and provides a corresponding detection signal; an alignment system adapted to selectively alter a location of the sensing area with respect to the flow chamber, wherein the alignment system is adapted to selectively change the location of the sensing area at a speed greater than the flow rate; and a control unit connected to the irradiation system, the detection system, and the alignment system, the control unit adapted to: cause the irradiation system to scan the irradiation spot during a first measurement interval; and (e.g., subsequently or otherwise), operate the alignment system to translate the location of the sensing area along the flow direction.

B: The flow cytometer according to paragraph A, wherein the control unit is further adapted to: detect the microparticulate sample using the detection signal provided by the detection optical system during the first measurement interval; after the operating, cause the irradiation system to scan the irradiation spot during a second measurement interval; and (e.g., subsequently or otherwise), detect the microparticulate sample using the detection signal provided by the detection optical system during the second measurement interval.

C: The flow cytometer according to paragraph B, further including a delivery system adapted to add a bio-effective substance to the carrier fluid.

D: The flow cytometer according to paragraph C, wherein the control unit is further adapted to operate the delivery system to add the bio-effective substance to the carrier fluid after the first measurement interval and before the second measurement interval.

E: The flow cytometer according to paragraph D, wherein the control unit is further adapted to determine an effect on the microparticulate sample of the bio-effective substance using the two detection signals.

F: The flow cytometer according to any of paragraphs A-E, wherein the control unit is adapted to cause the irradiation system to scan the irradiation spot during individual ones of one or more additional measurement intervals so that at least three detection signals are provided for the microparticulate sample.

G: The flow cytometer according to any of paragraphs A-F, wherein the alignment system includes a movable stage, the flow chamber is mounted to the stage, and the control unit is adapted to operate the alignment system to move the flow chamber opposite the flow direction using the stage.

H: The flow cytometer according to any of paragraphs A-G, wherein the alignment system includes a directing unit adapted to change a point of aim of the irradiation system and the control unit is adapted to operate the alignment system to change the point of aim along the flow direction.

I: The flow cytometer according to any of paragraphs A-H, further including a delivery system adapted to add a bio-effective substance to the carrier fluid.

J: The flow cytometer according to paragraph I, wherein the delivery system is adapted to add the bio-effective substance before or during the first measurement interval.

K: The flow cytometer according to any of paragraphs A-J, wherein the carrier fluid includes a plurality of the microparticulate samples, the flow chamber is configured so that the carrier fluid passes through the flow chamber as a substantially hydrodynamically planar flow, and the control unit is adapted to perform scanning and detection so that two detection signals are provided for each microparticulate sample.

L: The flow cytometer according to any of paragraphs A-K, wherein the flow chamber is adapted to permit a carrier fluid to flow through the flow channel along the flow direction at a flow rate, the carrier fluid including the microparticulate sample.

M: The flow cytometer according to any of paragraphs A-L, wherein the irradiation spot has a wavelength $\lambda$ and a full width at half maximum that is no larger than 2 µm, or smaller than $\lambda/0.1$, or between $\lambda/0.1$ and $\lambda/2.0$.

N: The flow cytometer according to any of paragraphs A-M, wherein the irradiation system includes an optical element through which at least some light of the irradiation spot passes, the optical element has a numerical aperture (NA), and the irradiation spot has a wavelength $\lambda$ and has a full width at half maximum substantially equal to $0.48 \times \lambda/\text{NA}$.

O: The flow cytometer according to any of paragraphs A-N, wherein the irradiation system is adapted to scan one or more additional irradiation spot(s) across respective sensing area(s) of the flow channel in respective scan direction(s) different from the flow direction.

P: The flow cytometer according to paragraph O, wherein the detection system is further adapted to detect respective time-varying intensit(ies) of respective resultant light from the sensing area(s) and provide corresponding additional detection signal(s).

Q: The flow cytometer according to paragraph P, wherein the control unit is further adapted to determine a speed of the microparticulate sample along the flow direction based at least in part on the detection signal and one or more of the additional detection signal(s).

R: The flow cytometer according to any of paragraphs O-Q, wherein the irradiation system includes an optical element arranged to receive light from a light source and provide the irradiation spot and the additional irradiation spot(s).

S: The flow cytometer according to paragraph R, wherein the optical element includes a diffractive optical element.

T: The flow cytometer according to any of paragraphs O-S, wherein the irradiation system is adapted to scan the irradiation spot and the additional irradiation spot(s) in fixed phase with respect to each other.

U: The flow cytometer according to any of paragraphs A-T, wherein the detection system is adapted to detect the resultant light including transmitted light.

V: The flow cytometer according to any of paragraphs A-U, wherein the irradiation optical system is configured to scan the irradiation spot forward and back across the scanning area and the detection system is adapted to provide the detection signal corresponding to both the forward scanning and the back scanning.

W: The flow cytometer according to any of paragraphs A-V, wherein the irradiation system includes a laser, and the irradiation spot is a laser spot.

X: The flow cytometer according to paragraph W, wherein the irradiation system includes a light deflector that deflects light from the laser substantially along the axis perpendicular to the flow direction of the microparticulate sample in the micro flow channel in order to scan the irradiation spot.

Y: The flow cytometer according to paragraph X, wherein the light deflector includes an acoustic optical deflector or an electro-optic deflector.

Z: The flow cytometer according to any of paragraphs A-Y, wherein the detection system includes a photo-multiplier tube (PMT), an avalanche photodetector (APD), or a silicon (Si) photodetector.

AA: A computer-readable medium, e.g., a computer storage medium, having thereon computer-executable instructions, the computer-executable instructions upon execution configuring a computer to perform operations of the control unit as recited in any of claims A-Z.

AB: A method of observing a microparticulate sample, the method comprising: passing the microparticulate sample through a flow chamber along a flow direction; scanning an irradiation spot smaller than the microparticulate sample across a sensing area of the flow chamber, the scanning comprising translating the irradiation spot substantially along a scan direction different from the flow direction; detecting, contemporaneously with scanning, a time-varying intensity of resultant light from the flow chamber and providing a corresponding first intensity signal of the microparticulate sample; subsequently, translating a relative position of the sensing area with respect to the flow chamber along the flow direction; and subsequently, repeating the scanning and detecting steps and providing a second intensity signal of the microparticulate sample.

AC: The method according to paragraph AB, wherein the passing includes providing a flow of carrier fluid through the flow chamber, the carrier fluid bearing the microparticulate sample.

AD: The method according to paragraph AC, further including, using a processor, automatically determining an image map of the microparticulate sample using the first and second detection signals and a flow rate of the flow of carrier fluid.

AE: The method according to paragraph AC or AD, further including hydrodynamically focusing the carrier fluid with the microparticulate sample into the sensing area.

AF: The method according to any of paragraphs AB-AE, further including, using a processor, automatically determining a property of the microparticulate sample by comparing the first and second intensity signals.

AG: The method according to any of paragraphs AB-AF, further including exposing the microparticulate sample to a bio-effective substance before the repeating of the scanning step.

AH: The method according to any of paragraphs AB-AG, wherein the microparticulate sample includes a living cell.

AI: The method according to any of paragraphs AB-AH, wherein the translating step includes moving the flow chamber substantially opposite the flow direction using a stage.

AJ: The method according to any of paragraphs AB-AI, wherein the translating step includes redirecting the irradiation spot substantially along the flow direction.

AK: The method according to any of paragraphs AB-AJ, wherein the scanning includes scanning a plurality of irradiation spots across respective sensing areas of the flow chamber in respective scan directions different from the flow direction.

AL: The method according to paragraph AK, wherein the detecting includes detecting respective time-varying intensities of resultant light from the sensing areas and providing corresponding intensity signals of the microparticulate sample.

AM: The method according to any of paragraphs AB-AL, further including automatically, using a processor, determining a flow rate of the microparticulate sample based at least in part on the first intensity signal and the second intensity signal.

AN: A computer-readable medium, e.g., a computer storage medium, having thereon computer-executable instructions, the computer-executable instructions upon execution configuring a computer to perform operations as any of claims AB-AM recites.

AO: A device comprising: a processor; and a computer-readable medium, e.g., a computer storage medium, having thereon computer-executable instructions, the computer-executable instructions upon execution by the processor configuring the device to perform operations as any of claims AB-AM describes.

AP: A system comprising: means for processing; and means for storing having thereon computer-executable instructions, the computer-executable instructions including means to configure the device to carry out a method as any of claims AB-AM describes.

AQ: A method of observing a microparticulate sample, the method comprising: passing the microparticulate sample through a flow chamber along a flow direction using a carrier fluid; scanning a plurality of irradiation spots, each smaller than the microparticulate sample, across respective sensing areas of the flow chamber along respective scan directions different from the flow direction; detecting, contemporaneously with scanning, respective time-varying intensities of respective resultant light from the flow chamber in the respective sensing areas and providing respective first intensity signals of the microparticulate sample; determining, using a processor, a first value comprising a lateral position of the microparticulate sample in the flow chamber and a speed of the microparticulate sample along the flow direction, wherein the first value is determined based at least in part on the respective first intensity signals.

AR: The method according to paragraph AQ, further including determining, using the processor, respective lateral position(s) of individual ones of one or more additional microparticulate sample(s) and respective speed(s) of individual ones of the one or more additional microparticulate sample(s) along the flow direction based at least in part on the respective first intensity signals.

AS: The method according to paragraph AQ or AR, further including: translating relative positions of the sensing areas with respect to the flow chamber along the flow direction; and subsequently, repeating the scanning and detecting steps to provide respective second intensity signals of the microparticulate sample.

AT: The method according to paragraph AS, wherein the translating includes moving the flow chamber substantially opposite the flow direction.

AU: The method according to paragraph AS or AT, wherein the translating step includes redirecting the irradiation spots substantially along the flow direction.

AV: The method according to any of paragraphs AS-AU, wherein the translating is performed at a translation speed based at least in part on the determined speed of the microparticulate sample.

AW: The method according to paragraph AV, wherein the translation speed is faster than the determined speed of the microparticulate sample.

AX: The method according to any of paragraphs AQ-AW, further including hydrodynamically focusing the carrier fluid with the microparticulate sample in the sensing areas.

AY: A computer-readable medium, e.g., a computer storage medium, having thereon computer-executable instructions, the computer-executable instructions upon execution configuring a computer to perform operations as any of claims AQ-AX recites.

AZ: A device comprising: a processor; and a computer-readable medium, e.g., a computer storage medium, having thereon computer-executable instructions, the computer-executable instructions upon execution by the processor configuring the device to perform operations as any of claims AQ-AX describes.

BA: A system comprising: means for processing; and means for storing having thereon computer-executable instructions, the computer-executable instructions including means to configure the device to carry out a method as any of claims AQ-AX describes.

BB: A system for imaging a microparticulate sample, the system comprising: a flow chamber including a flow channel formed therein to permit the microparticulate sample to travel in a flow direction along the flow channel; an irradiation system adapted to scan a plurality of irradiation spots, each smaller than the microparticulate sample, across respective sensing areas of the flow chamber along respective scan directions different from the flow direction; a detection system adapted to detect, contemporaneously with scanning, respective time-varying intensities of respective resultant light from the flow chamber in the respective sensing areas, and adapted to provide respective intensity signals of the microparticulate sample; and a processing unit adapted to automatically determine an image of the microparticulate sample based at least in part on the respective intensity signals.

BC: The system according to paragraph BB, wherein the processing unit is adapted to: determine a speed of the microparticulate sample along the flow direction based at least in part on the respective intensity signals; and adjust at least a scanning frequency of the plurality of irradiation spots or scanning phase(s) of one or more of the plurality of irradiation spots based at least in part on the determined speed of the microparticulate sample, wherein the adjusted scanning frequency or phase(s) cause individual ones of the plurality of irradiation spot(s) to have different spatial phases with respect to an axis of the microparticulate sample along the flow direction.

BD: The system according to paragraph BB or BC, further including a flow unit responsive to the processing unit to move the microparticulate sample through the flow chamber at a selected velocity, wherein the processing unit is adapted to adjust the selected velocity based at least in part on spacing(s) of individual ones of the irradiation spots so that individual ones of the plurality of irradiation spot(s) have different spatial phases with respect to an axis of the microparticulate sample along the flow direction.

BE: The system according to any of paragraphs BB-BD, wherein the processing unit is adapted to provide the image by aggregating the intensity signals, averaging the intensity signals, or computing difference(s) between individual ones of the intensity signals.

BF: The system according to any of paragraphs BB-BE, further including a fluid supply providing carrier fluid that carries the microparticulate sample through the flow chamber, wherein the flow chamber is configured so that the carrier fluid passes through the flow chamber as a substantially hydrodynamically planar flow.

BG: The system according to any of paragraphs BB-BF, the processing unit further adapted to adjust the intensity signals based on relative intensities of the plurality of irradiation spots and determine the image of the microparticulate sample based at least in part on the adjusted intensity signals.

BH: The system according to any of paragraphs BB-BG, wherein the sensing areas are arranged along the flow direction.

BI: A computer-readable medium, e.g., a computer storage medium, having thereon computer-executable instructions, the computer-executable instructions upon execution configuring a computer to perform operations of the processing unit as recited in any of claims BB-BH.

BJ: In a system including a hydrodynamically-planar flow chamber according to any of paragraphs K, AE, AX, or BF, the improvement comprising: components described in any of paragraphs A-AA, AN-AP, or AY-BI, or with reference to at least one of FIGS. 1-16; means or devices for performing functions described in any of paragraphs AB-AM or AQ-AX or with reference to at least one of FIGS. 1-16; or computer-readable media including instructions executable by processor(s) to cause the processor(s) to perform functions described in any of paragraphs AB-AM or AQ-AX or with reference to at least one of FIGS. 1-16.

CONCLUSION

The invention is inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The operations of the example processes are illustrated in individual blocks and summarized with reference to those blocks. The processes are illustrated as logical flows of blocks, each block of which can represent one or more operations that can be implemented in hardware, software, and/or a combination thereof. In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform particular functions and/or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more data-processing system(s) 101 such as one or more internal and/or external CPUs and/or GPUs, and/or one or more pieces of hardware logic such as FPGAs, DSPs, and/or other types described above.

All of the methods and processes described above can be embodied in, and fully automated via, software code modules executed by one or more computers and/or processors. The code modules can be embodied in any type of computer-readable medium. Some and/or all of the methods can be embodied in specialized computer hardware.

Conditional language such as, among others, "can," "could," "might" and/or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples and/or that one or more examples necessarily include logic for deciding, with and/or without user input and/or prompting, whether certain features, elements and/or steps are included and/or are to be performed in any particular example. The word "or" and the phrase "and/or" are used herein in an inclusive sense unless specifically stated otherwise. Accordingly, conjunctive language such as the phrases "X, Y, or Z," "at least X, Y, or Z," or "at least one of X, Y or Z," unless specifically stated otherwise, is to be understood as signifying that an item, term, etc., can be either X, Y, or Z, or a combination thereof.

Any routine descriptions, elements and/or blocks in the flow diagrams described herein and/or depicted in the attached figures should be understood as potentially representing modules, segments, and/or portions of code that include one or more executable instructions for implementing specific logical functions and/or elements in the routine. Alternative implementations are included within the scope of the examples described herein in which elements and/or functions can be deleted and/or executed out of order from any order shown or discussed, including substantially synchronously and/or in reverse order, depending on the functionality involved as would be understood by those skilled in the art. Examples herein are nonlimiting unless expressly stated otherwise, regardless of whether or not they are explicitly described as being nonlimiting. It should be emphasized that many variations and modifications can be made to the above-described examples, the elements of which are to be understood as being among other acceptable examples. All such modifications and variations are intended to be included herein within the scope of this disclosure and protected by the following claims. Moreover, in the claims, any reference to a group of items provided by a preceding claim clause is a reference to at least some of the items in the group of items, unless specifically stated otherwise.

What is claimed is:

1. An image flow cytometer for observing a microparticulate sample, the flow cytometer comprising:
    a flow chamber including a flow channel formed therein to permit the microparticulate sample to travel in a flow direction at a flow rate along the flow channel;
    an irradiation system adapted to scan an irradiation spot across a sensing area of the flow channel in a scan direction different from the flow direction;
    a detection system that detects a time-varying intensity of resultant light from the sensing area and provides a corresponding detection signal;
    an alignment system adapted to selectively alter a location of the sensing area with respect to the flow chamber, wherein the alignment system is adapted to selectively change the location of the sensing area at a speed greater than the flow rate; and
    a control unit communicatively connected to the irradiation system, the detection system, and the alignment system, the control unit adapted to:
        cause the irradiation system to scan the irradiation spot during a first measurement interval; and
        operate the alignment system to translate the location of the sensing area along the flow direction.

2. The flow cytometer according to claim 1, wherein the control unit is further adapted to:
    detect the microparticulate sample using the detection signal provided by the detection optical system during the first measurement interval;
    after the operating, cause the irradiation system to scan the irradiation spot during a second measurement interval; and
    detect the microparticulate sample using the detection signal provided by the detection optical system during the second measurement interval.

3. The flow cytometer according to claim 2, further including a delivery system adapted to add a bio-effective substance to the carrier fluid.

4. The flow cytometer according to claim 3, wherein the control unit is further adapted to operate the delivery system to add the bio-effective substance to the carrier fluid after the first measurement interval and before the second measurement interval.

5. The flow cytometer according to claim 1, wherein the alignment system includes a movable stage, the flow chamber is mounted to the stage, and the control unit is adapted to operate the alignment system to move the flow chamber substantially opposite the flow direction using the stage.

6. The flow cytometer according to claim 1, wherein the alignment system includes a directing unit adapted to change a point of aim of the irradiation system and the control unit is adapted to operate the alignment system to change the point of aim substantially along the flow direction.

7. The flow cytometer according to claim 1, wherein:
    the irradiation system is adapted to scan one or more additional irradiation spot(s) across respective sensing area(s) of the flow channel in respective scan direction(s) different from the flow direction;
    the detection system is further adapted to detect respective time-varying intensit(ies) of respective resultant light from the sensing area(s) and provide corresponding additional detection signal(s); and
    the control unit is further adapted to determine a speed of the microparticulate sample along the flow direction based at least in part on the detection signal and one or more of the additional detection signal(s).

8. A method of observing a microparticulate sample, the method comprising:
    passing the microparticulate sample through a flow chamber along a flow direction at a flow rate of the microparticulate sample;
    scanning an irradiation spot smaller than the microparticulate sample across a sensing area of the flow chamber, the scanning comprising translating the irradiation spot substantially along a scan direction different from the flow direction;
    detecting, contemporaneously with scanning, a time-varying intensity of resultant light from the flow chamber and providing a corresponding first intensity signal of the microparticulate sample;
    subsequently, translating a relative position of the sensing area with respect to the flow chamber along the flow direction at a speed greater than the flow rate of the microparticulate sample; and
    subsequently, repeating the scanning and detecting and providing a second intensity signal of the microparticulate sample.

9. The method according to claim 8, wherein:
    the passing includes providing a flow of carrier fluid through the flow chamber, the carrier fluid bearing the microparticulate sample; and
    the method further includes, using a processor, automatically determining an image map of the microparticulate sample using the first and second detection signals and a flow rate of the flow of carrier fluid.

10. The method according to claim 8, wherein the translating includes moving the flow chamber substantially opposite the flow direction using a stage.

11. The method according to claim 8, wherein the translating includes redirecting the irradiation spot substantially along the flow direction.

12. The method according to claim 8, wherein the scanning includes scanning a plurality of irradiation spots across respective sensing areas of the flow chamber in respective scan directions different from the flow direction.

13. A method of observing a microparticulate sample, the method comprising:
    passing the microparticulate sample through a flow chamber along a flow direction using a carrier fluid;
    scanning a plurality of irradiation spots, each smaller than the microparticulate sample, across respective sensing areas of the flow chamber along respective scan directions different from the flow direction;
    detecting, contemporaneously with scanning, respective time-varying intensities of respective resultant light from the flow chamber in the respective sensing areas and providing respective first intensity signals of the microparticulate sample;
    determining, using a processor, a first value comprising at least one of a lateral position of the microparticulate sample in the flow chamber and a speed of the microparticulate sample along the flow direction, wherein the first value is determined based at least in part on the respective first intensity signals.

14. The method according to claim 13, further including:
translating relative positions of the sensing areas with respect to the flow chamber along the flow direction; and
subsequently, repeating the scanning and detecting to provide respective second intensity signals of the microparticulate sample.

15. The method according to claim 14, wherein the translating includes moving the flow chamber substantially opposite the flow direction.

16. The method according to claim 14, wherein the translating includes redirecting the irradiation spots substantially along the flow direction.

17. The method according to claim 14, further comprising:
determining a translation speed based at least in part on the determined speed of the microparticulate sample; and
performing the translating substantially at the translation speed.

18. The method according to claim 17, wherein the translation speed is faster than the determined speed of the microparticulate sample.

19. The method according to claim 13, further including hydrodynamically focusing the carrier fluid with the microparticulate sample in the sensing areas.

20. The method according to claim 13, further comprising, using the processor, automatically determining an image of the microparticulate sample based at least in part on the first intensity signals.

* * * * *